United States Patent [19]

Komazawa et al.

[11] Patent Number: 6,046,289
[45] Date of Patent: Apr. 4, 2000

[54] PROPENAMIDE DERIVATIVES CONTAINING ARG-GLY-ASP POLYMERS OBTAINED THEREFROM

[76] Inventors: Hiroyuki Komazawa; Masayoshi Kojima; Atsushi Orikasa, all of c/o Fuji Photo Film Co., Ltd., 210 Nakanuma, Minami-Ashigara-shi, Kanagawa-ken, Japan

[21] Appl. No.: 08/278,251

[22] Filed: Jul. 20, 1994

Related U.S. Application Data

[63] Continuation of application No. 07/798,624, Nov. 26, 1991, abandoned.

[30] Foreign Application Priority Data

| Nov. 27, 1990 | [JP] | Japan | 2-324611 |
| Nov. 30, 1990 | [JP] | Japan | 2-334792 |
| Nov. 30, 1990 | [JP] | Japan | 2-334793 |
| Mar. 29, 1991 | [JP] | Japan | 3-066157 |
| Mar. 29, 1991 | [JP] | Japan | 3-066158 |
| Mar. 29, 1991 | [JP] | Japan | 3-066160 |

[51] Int. Cl.$^7$ .............. A61K 38/02; C08H 1/00; C07K 5/00

[52] U.S. Cl. ............... 526/238.1; 435/240.243; 530/332; 530/327; 530/328; 530/329; 530/330; 530/331; 530/345; 514/14; 514/15; 514/16; 514/17; 514/18

[58] Field of Search ............... 435/240.243; 526/238.1; 530/332, 327–331, 345; 514/14–18

[56] References Cited

U.S. PATENT DOCUMENTS

| 4,062,831 | 12/1977 | Kopecek | 260/47 |
| 4,097,470 | 6/1978 | Drobnik | 260/78 |
| 4,578,079 | 3/1986 | Ruoslahti | 623/11 |
| 5,278,063 | 1/1994 | Hubbell | 435/240.243 |
| 5,330,911 | 7/1994 | Hubbell | 435/240.243 |
| 5,362,831 | 11/1994 | Mongelli | 526/304 |

FOREIGN PATENT DOCUMENTS 0387975  9/1990  European Pat. Off. .

OTHER PUBLICATIONS

Tressler et al., *Cancer Commun.* 1, 55–63, 1989.
Saiki, I. *Jpn. J. Cancer. Res.* 81, 660, 1990.
Brandley (*Anal. Biochem.* 172, 270, 1988).
Pless (*J Biol Chem* 258, 2340, 1983).
Eckstein, *Chem. Pept. Proteins* 4, 61–68, 1989.
Bille *Eur. J. Biochem.*, 180, 41, 1989.
Eckstein, *Biopolymers* 25, 1055, 1986.

*Primary Examiner*—Cecilia J. Tsang
*Assistant Examiner*—David Lukton

[57] ABSTRACT

A propenamide derivative of the formula (I) having, as an essential structural unit, an adhesive peptide represented by the formula (II) in the side chain or salts thereof:

Formula (I): $R^1R^2C=CR^3-CO-[NH]-$
Formula (II): $-[R^4]-[CO]-([X]\text{-Arg-Gly-Asp-}[Y])_n-[Z]-[R^5]-$ wherein $R^1$ and $R^2$ each represents a hydrogen atom or a carboxyl group and $R^3$ represents a hydrogen or halogen atom, methyl, ethyl or carboxymethyl group; X and Y each represents an amino acid residue selected from the group consisting of Ser, Gly, Val, Asn and Pro or a peptide residue consisting of two or more of the amino acids; z represents $-O-$ or $-NH-$; one of $R^4$ and $R^5$ represents a hydrogen atom, and the other represents a linear or branched alkylene group having 1 to 11 carbon atoms or an arylene group having 6 to 11 carbon atoms wherein the alkylene and arylene groups may be substituted with one or more halogen atom, carbonyl, carboxyl, amino, hydroxyl, sulfo, aryl, nitro or cyano group, or unsaturated double or triple bond; n is an integer of from 1 to 5; and [ ] means that each corresponding group or residue therebetween may be present or absent. A copolymer and crosslinked copolymer of the derivative with an anionic or cationic monomer or additional polyfunctional polymer. The use of the compounds for inhibiting adhesion of animal cells, or coagulation•adhesion of blood platelets, or for cultivating animal cells.

14 Claims, No Drawings

PROPENAMIDE DERIVATIVES CONTAINING ARG-GLY-ASP POLYMERS OBTAINED THEREFROM

This is a Continuation of Parent Application Ser. No. 07/798,624, filed Nov. 26, 1991, now abandoned.

BACKGROUND OF THE INVENTION

The present invention relates to propenamide derivatives having a tripeptide, Arg-Gly-Asp, as an essential unit, polymers, copolymers and salts thereof as well as a composition for inhibiting adhesion of animal cells and a composition for inhibiting coagulation and/or adhesion of blood platelets. The present invention also relates to crosslinked polymers and crosslinked copolymers of the propenamide derivatives having a tripeptide, Arg-Gly-Asp, as an essential unit, and salts thereof as well as a substrate for cultivating animal cells.

Fibronectin is a protein involved in the cell-extracellular substrate adhesion and is likewise thought to be involved in coagulation of blood platelets and the metastasis of cancer. These interactions are mediated by a series of receptors present in the cell surface region, it is confirmed that these receptors can specifically recognize an amino acid sequence: Arg-Gly-Asp of the fibronectin although the fibronectin is a macromolecule having a molecular weight of about 250,000 and there has been reported that the sequence plays an important role in the interaction between the receptors and the fibronectin (Nature, 1984,309, p. 30). Since then, there have been conducted many studies in which an oligopeptide or polypeptide having such an amino acid sequence: Arg-Gly-Asp is used.

There have been reported various studies, such as a method for inhibiting the coagulation of blood platelets by the use of various linear and cyclic oligopeptides having an Arg-Gly-Asp sequence (Polymer Preprints, Japan, 1989,38, p. 3149; Japanese Unexamined Patent Publication (hereinafter referred to as "J.P. KOKAI") No. Hei 2-174797); a method in which a peptide having an Arg-Gly-Asp sequence is used as a cell movement-inhibiting agent (J.P. KOKAI No. Hei 2-4716); and a method using, as a cell-adhesive membrane, a PMMA film on which Arg-Gly-Asp sequences are immobilized (Polymer Preprints, Japan, 1988, 37, p. 705). In addition, J.P. KOKAI Nos. Hei 1-309682 and Hei 1-305960 disclose a method which comprises peptides having Arg-Gly-Asp sequences as essential structural units covalently bonded to a polymer and the resulting product is used as a substrate for cultivating animal cells or for biological composite artificial organs and J.P. KOKAI No. Sho 64-6217 discloses a method in which a polypeptide having Arg-Gly-Asp-Ser (SEQ ID NO:5) sequences is used as a platelet protective agent for blood taken out of the body. Further, there has been known a method comprising inhibiting the metastasis of cancer by the use of an oligopeptide having Arg-Gly-Asp sequences or a polypeptide having the sequence as repeating units (Int. J. Biol. Macromol., 1989, 11, p. 23; ibid, 1989, 11, p. 226; Jpn. J. Cancer Res., 1989, 60, p. 722).

A polymer generally has various properties and functions and therefore interactions between the polymer and a living body are significantly different from those between a low-molecular substance and a living body. There have been made many studies to link a low-molecular drug or a biologically active peptide to a polymer and to control interactions between the drug or the peptide and cells or behavior of the drug or the peptide in a living body. Such applications of polymers have widely been tried to the field of life sciences such as medical polymers, polymer drugs, materials for diagnosis, bioreactors, bioaffinity materials and the like. Such polymers and use thereof are detailed in "Polymers and medical treatments", by K. Takemoto, et. al. published by Mita Publishing, "Biotechnology Series, Immobilized Enzymes", by I. Senhata published by Kodansha and "Affinity Chromatography", by M. Yamazaki, et. al. published by Kodansha.

Propenamide derivatives prepared from propenoic acid derivatives have vinyl groups and easily polymerize or copolymerize with various anionic or cationic vinyl monomers to produce various polymers or copolymers which can be used for many purposes. It has been reported that an oligopeptide having Arg-Gly-Asp as an essential unit was introduced into a water-insoluble vinyl polymer. However, there have never been known a propenamide derivative which has an oligopeptide having Arg-Gly-Asp as an essential unit in the side chain, a water-soluble polymer thereof, a water-soluble anionic or cationic copolymer thereof and a hydrogel thereof, which are expected to have increased bonding ability to a receptor and increased stability in blood.

SUMMARY OF THE INVENTION

Accordingly, an object of the present invention is to provide a novel propenamide derivative having a tripeptide, Arg-Gly-Asp, as an essential unit, a polymer thereof, a copolymer thereof with an anionic or cationic monomer and a salt thereof.

Another object of the present invention is to provide a composition for inhibiting adhesion of animal cells, which comprises the propenamide derivative, the polymer, the copolymer or the salt as an effective component.

A further object of the present invention is to provide a composition for suppressing coagulation and/or adhesion of blood platelets, which comprises the propenamide derivative, the polymer, the copolymer or the salt as an effective component.

A further object of the present invention is to provide a crosslinked polymer of the propenamide derivative, a crosslinked copolymer of the propenamide derivative and the anionic or cationic monomer, and a salt thereof.

A still further object of the present invention is to provide a substrate for cultivating animal cells, which comprises the crosslinked polymer, the crosslinked copolymer or the salt thereof as an effective component.

The present invention provides a propenamide derivative of the following general Formula (I) or (II):

Formula (I)
$R^1R^2C=CR^3$—CO—{NH}—{$R^4$}—{CO}—({X}-Arg-Gly-Asp-{Y})$_n$-{Z}—H;

or

Formula (II)
H—{CO}—({X}-Arg-Gly-Asp-{Y})$_n$-{Z}-{$R^5$}—{NH}—CO—C($R^3$)=C$R^1R^2$ wherein $R^1$ and $R^2$ each represents a hydrogen atom or a carboxyl group and $R^3$ represents a hydrogen or halogen atom, methyl, ethyl or carboxymethyl group, X and Y each represents an amino acid residue selected from the group consisting of Ser, Gly, Val, Asn and Pro or a peptide residue consisting of two or more of the amino acids;

Z represents —O— or —NH—;

wherein $R^4$ and $R^5$ each represents a substituted or unsubstituted alkylene group having 1 to 11 carbon atoms or a substituted or unsubstituted arylene group having 6 to 11 carbon atoms, wherein the substituted alkylene and substituted arylene group is substituted with one or more member selected from the group consisting of halogen atom, carbonyl, carboxyl, amino, hydroxl, sulfonic acid, aryl, nitro and cyano group;

n is an integer of from 1 to 5; and

[ ] means that each corresponding group or residue therebetween may be present or absent.

The present invention provides a polymer of the propenamide derivative of the general formula (I).

The present invention also provides a copolymer of the propenamide derivative of the general formula (I) having, as an essential structural unit, an adhesive peptide represented by the General formula (IIA) or (II-b) in the side chain with an anionic monomer represented by the following general formula (III) and salts thereof:

Formula (III)

$H_2C=CR^6-[CO]-[W]-R^7$ wherein $R^6$ represents a hydrogen atom or a substituted or unsubstituted alkyl group having 1 to 3 carbon atoms; W represents —O— or —NH—; and $R^7$ represents a hydrogen atom or a linear or branched alkyl group having 1 to 12 carbon atoms or an aryl group having 6 to 11 carbon atoms wherein the alkyl and the aryl groups have at least one memeber selected from the group consisiting of carboxyl, sulfo and phosphoro groups and may have further substituent. [ ] means that each corresponding group or residue therebetween may be present or absent.

Examples of substituents on the alkyl represented by $R^6$ or the alkyl and the aryl represented by $R^7$ include halogen atom, carbonyl, carboxyl, amino, hydroxyl, sulfo, aryl, nitro and cyano groups, and double or triple bonds, two or more of which may be present in the same chain. Further, one or more bonds such as amide bond, ester bond, ether bond, urea bond, carbamate ester bond and carbonate ester bond may be present in the same chain. Moreover, a hetero ring may be present in the same chain.

The present invention also provides a copolymer of the propenamide derivative of the general formula (I) having, as an essential structural unit, an adhesive peptide represented by the general formula (II-a) or (II-b) in the side chain with a cationic monomer represented by the following general formula (IV) and salts thereof:

Formula (IV)

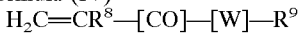

$H_2C=CR^8-[CO]-[W]-R^9$ wherein $R^8$ represents a hydrogen atom or a substituted or unsubstituted alkyl group having 1 to 3 carbon atoms, wherein the alkyl group may be substituted with one or more of halogen atom, carbonyl, amino, hydroxyl, nitro and cyano groups;

W represents —O— or —NH—; and $R^9$ represents a hydrogen atom or a linear or branched alkyl group having 1 to 12 carbon atoms or an aryl group having 6 to 12 carbon atoms wherein the alkyl and the aryl groups have at least one member selected from the group consisiting of amino, imino, amidino, quaternary ammonium and ammonium groups and may have further substituent.

[ ] means that each corresponding group or residue therebetween may be present or absent.

Examples of substituents on the alkyl represented by $R^8$ or the alkyl and the aryl represented by $R^9$ include halogen atom, quaternary ammonium, carbonyl, amino, imino, nitrilo, amidino, hydroxyl, aryl, nitro and cyano groups, and unsaturated double or triple bonds, two or more of which may be present in the same chain. Further, one or more bonds such as amide bond, ester bond, ether bond, urea bond, carbamate ester bond and carbonate ester bond may be present in the same chain. Moreover, a hetero ring such as pyridine and imidazole may be present in the same chain.

The present invention provides a composition for inhibiting adhesion of animal cells, which comprises at least one member selected from the group consisting of the propenamide derivatives, the polymers, the copolymers or the salts as an effective component.

The present invention provides a composition for suppressing coagulation and/or adhesion of blood platelets, which comprises at least one member selected from the group consisting of the propenamide derivatives, the polymers, the copolymers or the salts as an effective component.

The present invention provides a crosslinked polymer of the propenamide derivative, a crosslinked copolymer of the propenamide derivative and the anionic or cationic monomer, and a salt thereof.

The present invention provides a substrate for cultivating animal cells, which comprises at least one member selected from the group consisting of the crosslinked polymers, the crosslinked copolymers or the salts thereof as an effective component.

DETAILED DESCRIPTION OF THE INVENTION (a) Propenamide derivatives

Examples of a monomer which is to be bonded to N-terminal of the peptide fragment having Asp-Gly-Arg as an essential unit include propenamide derivatives having α-, β-, γ- or ω-amino acid residue such as N-methacryloylglycine, N-methacryloyl-β-alanine, N-methacryloylalanine, N-methacryloyl-γ-aminobutyric acid, N-methacryloylvaline, N-methacryloylnorleucine, N-methacryloylserine, N-methacryloylthreonine, N-methacryloylmethionine, N-methacryloylphenylalanine, N-methacryloyltyrosine, N-α-methacryloyltryptophane, N-methacryloylproline, N-methacryloylaspartic acid, N-methacryloylasparagine, N-methacryloylglutamic acid, N-methacryloylglutamine, N-α-methacryloylarginine and N-α-methacryloylcitrulline.

Preferred are N-methacryloylglycine, N-methacryloyl-β-alanine, N-methacryloylalanine, N-methacryloyl-β-aminopropionic acid, N-methacryloyl-γ-aminobutyric acid, N-methacryloylvaline, N-methacryloylleucine, N-methacryloylisoleucine, N-methacryloylnorvaline and N-methacryloylnorleucine.

Examples of a monomer which is to be bonded to C-terminal of the peptide fragment having Asp-Gly-Arg as an essential unit include mono-methacrylamides of alkylene diamines and arylene diamines. Preferred are ethylenediamine mono-methacrylamide, 1,3-diaminopropane mono-methacrylamide, 1,4-diaminobutane mono-methacrylamide and 1,6-diaminohexane mono-methacrylamide.

(b) Polymers of the propenamide derivatives

The present invention provides a polymer of the propenamide derivatives or salts thereof. The polymer may be prepared by radical polymerization of the propenamide derivatives or salts thereof. The polymer has a molecular weight of preferably not more than 300,000, more preferably 3,000 to 200,000 and is preferably soluble in water at room temperature.

(c) Copolymers of the propenamide derivatives with anionic or cationic monomers and salts thereof Anionic monomers used in the present invention are conventional polymerizable vinyl monomers but not limited to specific ones. Examples of the anionic monomers include vinyl monomers having carboxyl or sulfonic group such as acrylic acid, methacrylic acid, itaconic acid, maleic acid, fumaric acid, crotonic acid, 2-acrylamidoglycolic acid, 2-methacrylamidoglycolic acid, styrenesulfonic acid, vinylsulfonic acid, 2-acrylamido-2-methylpropanesulfonic amide and 4-vinylbenzoic acid; N-methacryloyl and N-acryloyl derivatives of 5-aminovaleric acid, 6-amino caproic acid and 12-amino lauric acid.

Further examples include vinyl monomers having amino acid residues such as N-methacryloylglycine, N-methacryloyl-β-alanine, N-methacryloylalanine, N-methacryloyl-γ-aminobutyric acid, N-methacryloylvaline, N-methacryloylleucine, N-methacryloylisoleucine, N-methacryloylnorvaline, N-methacryloylnorleucine, N-methacryloylserine, N-methacryloylthreonine, N-methacryloylmethionine, N-methacryloylphenylalanine, N-methacryloyltyrosine, N-α-methacryloyltryptophane, N-methacryloylproline, N-methacryloylhydroxyproline, N-methacryloylaspartic acid, N-methacryloylasparagine, N-methacryloylglutamic acid, N-methacryloylglutamine, N-α-methacryloylarginine, N-α-methacryloylcitrulline, N-acryloylglycine, N-acryloyl-β-alanine, N-acryloylalanine, N-acryloyl-γ-aminobutyric acid, N-acryloylvaline, N-acryloylleucine, N-acryloylisoleucine, N-acryloylnorvaline, N-acryloylnorleucine, N-acryloylserine, N-acryloylthreonine, N-acryloylmethionine, N-acryloylphenylalanine, N-acryloyltyrosine, N-α-acryloyltryptophane, N-acryloylproline, N-acryloylhydroxyproline, N-acryloyl-aspartic acid, N-acryloylasparagine, N-acryloylglutamic acid, N-acryloylglutamine, N-α-acryloylarginine and N-α-acryloylcitrulline.

Further examples include vinyl monomers having phosphoric group in the side chain such as methacryloyloxyethylphosphoric acid, methacryloyloxyethylphenylphosphoric acid and methacryloyloxydecanoylphosphoric acid.

Preferred are N-methacryloyl derivatives and N-acryloyl derivatives of glycine, β-alanine, 4-aminobutyric acid, 5-aminovaleric acid, 6-aminocaproic acid, 12-aminolauric acid, 4-aminobenzoic acid, leucine and glutamic acid; acrylic acid, methacrylic acid, itaconic acid and maleic acid.

Cationic monomers used in the present invention are conventional polymerizable vinyl monomers but not limited to specific ones. Examples of the cationic monomers include vinyl monomers having quaternary ammonium group such as chlorotrimethylammonioethyl methacrylamide, sulfotrimethylammonioethyl methacrylate, chlorotrimethylammonioethyl methacrylate, sulfoethyldimethylammonioethyl methacrylate, chloroethyldimethyl-ammonioethyl methacrylate, diallyldimethylammonium chloride, diallyldiethylammonium chloride, chlorotrimethylammoniopropyl acrylamide, chloroethyldimethylammoniopropyl acrylamide, trimethylammonioethyl acrylamide, sulfotrimethylammonioethyl acrylate, chlorotrimethylammonioethyl acrylate, sulfoethyldimethylammonioethyl acrylate, chloroethyldimethylammonioethyl acrylate, chlorotirmethylammoniopropyl acrylamide and chloroethyldimethylammoniopropyl acrylamide.

Further, there can be used vinyl monomers having a hetero ring in the side chain such as vinylpyridines and vinylimidazoles and vinyl monomers having an amino group such as dimethylaminoethyl methacrylate, diethylaminoethyl methacrylate, dimethylaminopropyl methacrylate, diethylaminopropyl methacrylate, dimethylaminoethyl methacrylamide and dimethylamninoethyl acrylamide.

Preferred are methacrylic acid derivatives such as chlorotrimethylammonioethyl methacrylamide, chlorotrimethyl-ammoniopropyl methacrylamide, chlorotrimethylammonioethyl methacrylate, dimethylaminoethyl methacrylamide, dimethylaminopropyl methacrylamide, dimethylamninoethyl methacrylate and dimethylamninopropyl methacrylate and acrylic acid derivatives having similar side chain groups.

The copolymers of the propenamide derivatives with the anionic or cationic monomer and salts thereof have a molecular weight of preferably not more than 300,000, more preferably 3,000 to 200,000 and is preferably soluble in water at room temperature.

The content of the unit derived from the propenamide derivative in the copolymers is preferably 0.1 to 90 mol %, more preferably 0.5 to 60 mol %.

(d) Crosslinked polymers of the propenamide derivatives, crosslinked copolymers of the propenamide derivatives with anionic or cationic monomers and salts thereof The present invention provides a crosslinked polymer of the above mentioned propenamide derivatives, a crosslinked copolymer of the propenamide derivatives with the anionic or cationic monomer and salts thereof. The crosslinked polymer and the crosslinked copolymer are preferably in the form of a hydrogel in an aqueous solution.

When the crosslinked polymer or copolymer is prepared, a polyfunctional monomer is added in addition to the propenamide derivative and the anionic or cationic monomer. Examples of the polyfunctional monomer include dimethacrylates, diacrylates, dimethacrylamides and diacrylamides such as triethyleneglycol dimethacrylate and methylene bisacrylamide; those having aromatic rings such as divinyl benzene; and those having the cell adhesive fragments.

The content of the unit derived from the polyfunctional monomer in the crosslinked polymer or the crosslinked copolymer is preferably 0.1 to 30 mol %, more preferably 0.5 to 20 mol %.

The content of the unit derived from the propenamide derivatives in the crosslinked copolymer is preferably 0.1 to 90 mol %, more preferably 0.5 to 60 mol %. The content of the unit derived from the polyfunctional monomer in the crosslinked copolymer is preferably 0.1 to 30 mol %, more preferably 0.5 to 20 mol %.

A crosslinked copolymer in the form of a hydrogel having different water content or gel strength can be prepared by the use of different amounts of the polyfunctional monomer.

Amino acids constituting the adhesive peptides according to the present invention may be L- or D-type; but preferably L-type.

Examples of salts of the propenamide derivatives, the polymers of the propenamide derivatives, the copolymers of the propenamide derivatives with an anionic monomer, the copolymers of the propenamide derivatives with a cationic monomer, the crosslinked polymers and the crosslinked copolymers of the present invention include inorganic acid salts such as hydrochlorides, sulfates, nitrates, phosphates and borates and organic acid salts such as acetates, trifluoroacetates, trifluoromethanesulfonates, lactates and tartrates.

Methods for synthesizing these peptides are not restricted to specific ones and may be liquid phase and solid phase methods and those in which an automatic synthesizer is employed. These synthesis methods are detailed in, for instance, Lectures on Biochemical Experiments, "Chemistry of Proteins IV", pp. 207–495, edited by Biochemical Society of Japan, published by Tokyo Kagaku Dojin Publishing Company; Lectures on Biochemical Experiments, Second Series, "Chemistry of Proteins (the last volume)", edited by Biochemical society of Japan, published by Tokyo Kagaku Dojin Publishing Company; and "Fundamental Knowledge and Experiments of Peptide Synthesis", edited by Izumiya et al., published by Maruzen Publishing Company. Alternatively, it is also possible to use commercially available synthetic peptides.

In order to couple the propenamide derivative with a cell adhesive peptide or to couple the propenamide derivative and an aminoalkyl carboxylic acid with a cell adhesive peptide, there can be used amide bond-forming methods such as an active ester method, a mixed acid anhydride method, an azide method, an acid chloride method, a symmetric acid anhydride method, a DCC method, a DCC-additive method, a carbonyldiimidazole method. The polymers and the crosslinked polymers of the propenamide derivatives and the copolymers and the crosslinked copolymers of the propenamide derivatives with anionic or cationic monomers can be prepared by conventional radical polymerization or ionic polymerization. Water-soluble polymers can be separated into fractions having different molecular weights by gel permeation chromatography or dialysis.

(e) Composition for inhibiting adhesion of animal cells and composition for inhibiting coagulation and/or adhesion of blood platelets The present invention further provides a composition for inhibiting adhesion of animal cells and a composition for inhibiting coagulation and/or adhesion of blood platelets, which comprises as an effective component at least one member selected from the group consisting of the propenamide derivatives, the polymers thereof, the copolymers of the derivatives and the anionic monomers, the copolymers of the, derivatives and the cationic monomers and salts thereof.

The derivatives, the polymers thereof, the copolymers thereof with anionic or cationic monomers or salts thereof of the invention have a core sequence: Arg-Gly-Asp of a cell-adhesive protein and are adhered to cells through the core sequence according to a mechanism similar to that for the cell-adhesive protein. For this reason, they serve as agonists or antagonists of the cell-adhesive protein which exhibit a variety of biological activities such as immunoregulating action, wound-healing action, action for inhibiting platelet coagulation observed in blood vessels and nervous disorder-healing action.

Thus, at least one of the propenamide derivatives, the polymers thereof, the copolymers thereof with anionic or cationic monomers or salts thereof of the invention can be administered to patients together with commonly used optional carriers or pharmaceutical auxiliary agents in the form of wound-healing agents, immunoregulating agents or platelet coagulation and/or adhesion-inhibiting agents. In particular, the derivatives are preferably used as animal cell adhesion-inhibiting agents or platelet coagulation and/or adhesion-inhibiting agents. The dose thereof varies depending on various factors such as conditions to be treated, age and weight of patients and generally ranges from 0.2 $\mu$g/kg to 400 mg/kg.

The derivatives, the polymers thereof, the copolymers thereof with anionic or cationic monomers or salts thereof may be administered through various routes which are generally used, for the administration of peptide-containing medicines. For instance, they are preferably administered parenterally, intravenously, intramuscularly and subcutaneously. In the preparation of injectable pharmaceutical preparations, the derivatives, the polymers thereof, the copolymers thereof with anionic or cationic monomers or salts thereof are dissolved in, for instance, PBS or physiological saline to give injectable solutions. These pharmaceutical preparations may comprise a commonly used stabilizer such as glycine and albumin. Moreover, the derivatives, the polymers thereof, the copolymers thereof with anionic or cationic monomers or salts thereof may be parenterally administered by encapsulating them in liposomes to give microcapsules or formulating them in the form of microsphere or hydrogel. Further, if they are formulated in the form of, for instance, suppository, sublingual tablets and nasal sprays, they can be absorbed through mucous other than digestive tracts.

(f) Substrates for cultivating animal cells

The present invention provides a substrate for cultivating animal cells which comprises as an effective component at least one member selected from the group consisting of the crosslinked polymers of the propenamide derivatives, the crosslinked copolymers of the derivatives and the anionic monomers, the crosslinked copolymers of the derivatives and the cationic monomers and salts thereof.

Methods for the use of the substrate for cultivating animal cells in cultivating the animal cells are conventional ones but not restricted to specific ones. For example, there may be mentioned a method for cultivating animal cells wherein the animal cells are suspended in a culture solution containing beads to which an adhesive peptide has been covalently bonded and the suspension is stirred at a low speed to make the animal cells adhere to the surface of the beads or micro carriers on which the cells are cultured; a method for cultivating animal cells wherein the animal cells are cultured on a laboratory dish-roller bottle to which an adhesive peptide has been covalently bonded; a method for cultivating animal cells wherein a culture solution is circulated through hollow fibers to which an adhesive peptide has been covalently bonded to make the cells adhere to the internal surface of the hollow fibers on which the cells are cultured; and a method for cultivating animal cells wherein a column charged with micro carriers to which an adhesive peptide has been covalently bonded is used.

The substrate for cultivating animal cells of the present invention can be used for cultivating various animal cells such as cells derived from a living body and hybridomas.

The present invention will hereinafter be explained in more detail with reference to the following non-limitative working Examples and Preparation Examples, but the present invention is by no means limited to these specific Examples.

In the present specification, Arg is referred to as R, Gly is G, Asp is D, Ser is S and Pro is P. Protective groups and agents used are abbreviated as follows.

Boc: t-butoxycarbonyl
OBzl: benzyl ester
HOBt: hydroxybenzotriazole
OSu: N-hydroxysuccinimide
ONb: nitrobenzyl ester
TFA: trifluoroacetic acid
DCC: dicyclohexylcarbodiimide
DCurea: cyclohexylurea
Mts: mesitylenesulfonyl
DMF: dimethylformamide
4Abu: 4-aminobutyric acid

PREPARATION EXAMPLE 1

Carboxyethyl methacrylamide was prepared by Schotten-Baumann reaction as follows. Methacrylic chloride 20.9 g (0.2 mol) was dropwise added to a sodium hydroxide solution of β-alanine 17.8 g (0.2 mol) under ice cooling, stirred for 4 hours and neutralized with hydrochloric acid.

The mixture was concentrated under reduced presssure and sodium chloride precipitated was separated by filtration. The concentrate was extracted with chloroform. The extract was dried and concentrated under reduced pressure to evaporate chloroform. The residue was washed with ether to obtain Preparation product 1 as white powder (17.6 g, yield: 56%).
Preparation product 1

$CH_2=CCH_3-CO-NH-C_2H_4-COOH$

PREPARATION EXAMPLES 2 TO 8

In the same manner as in Preparation Example 1, acrylic chloride, methacrylic chloride or ethacrylic chloride was reacted with 4-aminobutyric acid, 5-aminovaleric acid, 6-aminocaproic acid, 12-aminolauric acid, leucine, glutamine or p-aminobenzoic acid to obtain the following propenoic acid derivatives.

Preparation product 2

$CH_2=CH-CO-NH-(CH_2)_3-COOH$ (yield: 52%)

Preparation product 3

$CH_2=CC_2H_5-CO-NH-(CH_2)_4-COOH$ (yield: 61%)

Preparation product 4

$CH_2=CCH_3-CO-NH-(CH_2)_5-COOH$ (yield: 69%)

Preparation product 5

$CH_2=CH-CO-NH-(CH_2)_{11}-COOH$ (yield: 71%)

Preparation product 6

$CH_2=CH-CO-NH-CH(CH_2CH(CH_3)_2)-COOH$ (yield: 64%)

Preparation product 7

$CH_2=CCH_3-CO-NH-CH(C_2H_4\ CONH_2)-COOH$ (yield: 59%)

Preparation product 8

$CH_2=CH-CO-NH-p-C_5H_4-COOH$ (yield: 68%)

Preparation product 9

$CH_2=CCH_3-CO-NH-CH_2-COOH$ (yield: 63%)

Preparation product 10

$CH_2=CCH_3-CO-NH-CH(C_2H_4COOH)-COOH$ (yield: 57%)

PREPARATION EXAMPLE 11

Aminoethyl methacrylamide was prepared by Schotten-Baumann reaction as follows. Methacrylic chloride 20.9 g (0.2 mol) was dropwise added to 400 ml of a chloroform solution of ethylenediamine 120 g (2 mol) under ice cooling and stirred for 4 hours. The mixture was concentrated under reduced presssure and 50 ml of a 5% sodium hydrogen carbonate solution was added. The mixture was extracted with 50 ml of chloroform. The extract was dried over sodium sulfate and concentrated. The residue was purified on an alumina column chromatography (eluant: chloroform/methanol=7/3) to obtain the target compound.

Preparation product 11

$CH_2=CCH_3-CO-NH-C_2H_4-NH_2$

Yield 14.8 g (57.8%, 0.116 mol)

PREPARATION EXAMPLE 12

Carboxyethyl methacrylamide prepared in Preparation Example 1 was polymerized by radical polymerization.

Carboxyethyl methacrylamide (2 g) was dissolved in 20 ml of DMF. A radical polymerization initiator V65 (2,2-azobis(2,4-dimethylvaleronitrile))(10 mg, available from WAKO PURE CHEMICALS) was added and polymerization was conducted at 65° C. for 4 hours under nitrogen atmosphere. The polymer was precipitated by ethyl acetate and dialyzed through Spectrapore 7 (fractional molecular weight: 3,000) against pure water to remove low molecular fractions followed by lyophilization to obtain Preparation product 12 (yield: 1.24 g).

A molecular weight was determined on TSKgel G3000SW column (available from TOSO Co., Ltd.)(mobile phase: 0.2 M phosphate buffer of pH 7.4, flow rate: 1.0 ml/min). PEG reduced molecular weight of the product was 30,000.

PREPARATION EXAMPLE 13

Carboxyethyl methacrylamide prepared in Preparation Example 1 was polymerized by radical polymerization to obtain a hydrogel.

A pair of silane treated glass plates (5 cm×6 cm×1 cm) and a gasket were provided. Carboxyethyl methacrylamide (2 g) and methylene bisacrylamide (100 mg: 5 wt %) were dissolved in 12 ml of distilled water and adjusted to pH 7.4 by 1 N NaOH. Ammonium persulfate (10 mg) was added and a nitrogen gas was supplied through the mixture to remove air therein. The mixture was injected between the glass plates which were then vised. Polymerization was conducted at 60° C. for 20 hours. A hydrogel produced was washed with distilled water to remove unreacted monomer. The gel (Preparation product 13) was sterilized by an ultraviolet lamp before it was used for cultivating animal cells.

PREPARATION EXAMPLE 14

Synthesis of trimethylammonioethyl methacrylamide

Dimethylethylenediamine (20.2 g, 0.23 mol) was dissolved in 100 ml of chloroform. Methacryloyl chloride (24 g, 0.23 mol) was dropwise added under ice cooling and stirred for 4 hours and then chloroform was evaporated. A methanol solution of 0.23 mol sodium hydroxide was added, stirred and filtered. The precipitate was separated by filtration and a methnol solution (10 ml) of methyl iodide (42.6 g, 0.3 mol) was added to the filtrate and stirred at room temperature for 2 hours. The mixture was concentrated under reduced pressure and converted to chloride in a diluted hydrochloric acid solution. The hydrochloride was recrystalized from water-methanol to obtain trimethylammonioethyl methacrylamide, Preparation product 14 (31.3 g, yield: 66%).

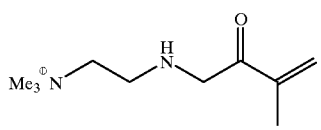

PREPARATION EXAMPLE 15

Preparation product 15

BocArg(Mts) (45.6 g, 0.1 mol) was dissolved in one liter of DMF. DCC (20.6 g, 0.1 mol) and HOBt (15 g, 0.11 mol) were added under ice cooling. Aminoethyl methacrylamide (12.8 g, 0.1 mol) prepared in Preparation Example 11 was added and stirred at 5° C. overnight. DCurea was removed by filtration and the mixture was concentrated under reduced pressure to remove DMF. The residue was dissolve in ethyl acetate. The solution was washed with an aqueous $NaHCO_3$ solution, 1 M citric acid solution and water, dried over $Na_2SO_4$ and evaporated to dryness. The product was reacted in 1 M trifluoromethanesulfonic acid-thioanisole-m-cresol solution in TFA under ice cooling for one hour and poured into ether. The oily product was dissolved in distilled water, washed with ethyl acetate, passed through an anion-exchange resin column (Amberlite IRA-400; Cl type) to change it to a hydrochloride and lyophilized to obtain Preparation product 15, as white solid (14.3 g, yield: 40%).

PREPARATION EXAMPLE 16

Chlorotrimethylammonioethyl methacrylamide prepared in Preparation Example 14 was polymerized by radical polymerization.

Chlorotrimethylammonioethyl methacrylamide (2 g) was dissolved in 20 ml of DMF. A radical polymerization initiator V65 (2,2-azobis(2,4-dimethylvaleronitrile))(10 mg, available from WAKO PURE CHEMICALS) was added and polymerization was conducted at 65° C. for 4 hours under nitrogen atmosphere. The polymer was precipitated by ethyl acetate and dialyzed through Spectrapore 7 (fractional molecular weight: 3,000) against pure water to remove low molecular fractions followed by lyophilization to obtain Preparation product 16 (yield: 1.08 g).

A molecular weight was determined on TSKgel G3000SW column (available from TOSO Co., Ltd.)(mobile phase: 0.2 M phosphate buffer of pH 7.4, flow rate: 1.0 ml/min). PEG reduced molecular weight of the product was 28,000.

PREPARATION EXAMPLE 17

Chlorotrimethylammonioethyl methacrylamide prepared in Preparation Example 14 was polymerized by radical polymerization to obtain a hydrogel.

A pair of silane treated glass plates (5 cm×6 cm×1 cm) and a gasket were provided. Chlorotrimethylammonioethyl methacrylamide (2 g) and methylenebisacrylamide (100 mg: 5 wt %) were dissolved in 12 ml of distilled water and adjusted to pH 7. 4 by 1 N NaOH. Ammonium persulfate (10 mg) was added and a nitrogen gas was supplied through the mixture to remove air therein. The mixture was injected between the glass plates which were then vised. Polymerization was conducted at 60° C. for 20 hours. A hydrogel produced was washed with distilled water to remove unreacted monomer. The gel (Preparation product 17) was sterilized by an ultraviolet lamp before it was used for cultivating animal cells.

SYNTHETIC EXAMPLES 1 TO 14

Synthesis of Adhesive Peptide by Solid Phase Method

Synthesis of this peptide was performed using a peptide synthesizer according to the Merrifield System. α-Amino groups were protected with Boc to obtain the oligopeptide having Arg-Gly-Asp as an essential unit. To the N terminal of the peptide, there were bonded by condensation reaction the propenoic acid derivatives prepared in Preparation Examples 1 to 10, acrylic acid, methacrylic acid or ethacrylic acid. Trifl uoromethanesulfonic acid was used to cleave the target products from the resin and to remove the protective groups in the side chains. The products were purified on a preparative high performance liquid chromatograph (HPLC) to obtain the propenamide derivatives showing a single peak which were then passed through an anion exchange column (Amberlite IRA-400; Cl type) to convert them into hydrochlorides.

Synthetic product 1
$CH_2=CH-CO-NH-(CH_2)_3-CO-RGD$ (SEQ ID NO:1)
Yield 35%
Amino acid analysis (nmol/50 μl)
R: 0.9982
G: 1.0319
D: 0.9971
4Abu: 1.0240
Mass spectrum $M^+$: 486

Synthetic product 2
$CH_2=CCH_3-CO-NH-C_2H_4-CO-(RGD)_2$ (SEQ ID NO:2)
Yield 24%
Amino acid analysis (nmol/50 μl)
R: 1.9568
G: 2.1004
D: 1.9673
β-alanine: 1.0257
Mass spectrum $M^+$: 815

Synthetic product 3
$CH_2=CCH_3-CO-NH-C_2H_4-CO-(RGD)_3$ (SEQ ID NO:3)
Yield 17%
Amino acid analysis (nmol/50 μl)
R: 2.8382
G: 3.1121
D: 2.9451
β-alanine: 1.0287
Mass spectrum $M^+$: 1144

Synthetic product 4
$CH_2=CCH_3-CO-NH-C_2H_4-CO-(RGD)_5$ (SEQ ID NO:4)
Yield 10% .
Amino acid analysis (nmol/50 μl)
R: 4.8664
G: 5.1965
D: 4.9033
β-alanine: 1.0449
Mass spectrum $M^+$: 1802

Synthetic product 5
$CH_2=CH-CO-NH-(CH_2)_3-CO-RGDS$ (SEQ ID NO:5)
Yield 33%
Amino acid analysis (nmol/50 μl)
R: 0.9989
G: 1.1008
D: 0.9596
S: 0.8991
4Abu: 1.0054
Mass spectrum $M^+$: 573

Synthetic product 6
$CH_2=CC_2H_5-CO-NH-(CH_2)_4-CO-RGDS$ (SEQ ID NO:6)
Yield 31%
Amino acid analysis (nmol/50 μl)
R: 0.9874
G: 0.9927
D: 0.9935
S: 0.8869
Mass spectrum $M^+$: 615

Synthetic product 7
CH$_2$=CCH$_3$—CO—NH—(CH$_2$)$_5$—CO-RGDS (SEQ ID NO:6)
Yield 30%
Amino acid analysis (nmol/50 µl)
R: 0.9755
G: 1.0361
D: 0.9671
S: 0.8943
Mass spectrum M$^+$: 615

Synthetic product 8
CH$_2$=CH—CO—NH—(CH$_2$)$_{11}$—CO-RGDS (SEQ ID NO:6)
Yield 27%
Amino acid analysis (nmol/50 µl)
R: 0.9647
G: 1.0570
D: 0.9884
S: 0.8603
Mass spectrum M$^+$: 686

Synthetic product 9
CH$_2$=CH—CO—NH—CH(CH$_2$ CH(CH$_3$)$_2$)—CO-RGDS (SEQ ID NO:7)
Yield 31%
Amino acid analysis (nmol/50 µl)
R: 0.9814
G: 1.0519
D: 0.9731
S: 0.8989
leucine: 0.9853
Mass spectrum M$^+$: 60

Synthetic product 10
CH$_2$=CCH$_3$—CO—NH—CH(C$_2$H$_4$CONH$_2$)—CO-RGDS (SEQ ID NO:8)
Yield 33%
Amino acid analysis (nmol/50 µl)
R: 0.9771
G: 1.0501
D: 0.9651
S: 0.8969
glutamic acid: 0.9587
Mass spectrum M$^+$: 630

Synthetic product 11
CH$_2$=CH—CO—NH—p—C$_6$H$_4$—CO-RGDS (SEQ ID NO:6)
Yield 31%
Amino acid analysis (nmol/50 µl)
R: 0.9845
G: 1.0361
D: 0.9554
S: 0.8879
Mass spectrum M$^+$: 595

Synthetic product 12
CH$_2$=CC$_2$H$_5$—CO—NH—(CH$_2$)$_4$—CO-GRGDS (SEQ ID NO:9)
Yield 35%
Amino acid analysis (nmol/50 µl)
R: 0.9582
G: 2.0371
D: 0.9874
S: 0.8733
Mass spectrum M$^+$: 672

Synthetic product 13
CH$_2$=CCH$_3$—CO-GRGDSP (SEQ ID NO:10)
Yield 26%
Amino acid analysis (nmol/50 µl)
R: 0.9669
G: 2.0552
D: 0.9809
S: 0.8677
P: 0.9546
Mass spectrum M$^+$: 656

Synthetic product 14
CH$_2$=CH—CO-GGGRGDS (SEQ ID NO:11)
Yield 30%
Amino acid analysis (nmol/50 µl)
R: 0.9554
G: 4.0011
D: 0.9380
S: 0.8518
Mass spectrum M$^+$: 659

SYNTHETIC EXAMPLE 15

Synthetic product 15
CH$_2$=CCH$_3$—CO—NH—C$_2$H$_4$—CO-RGDS (SEQ ID NO:12)

Synthetic product 15 was synthesized by a liquid phase method according to a sequential-extension method.

(1) Synthesis of BocSer(Bzl)OBzl

BocSer(Bzl) 60 g (0.2 mol) was added to 400 ml of ethyl acetate, to which triethylamine 21 g (0.2 mol) and benzyl bromide 35.4 g (0.2 mol) were added and reacted under refluxing condition for 4 hours. After cooled, the salt produced was separated by filtration. The filtrate was washed with an aqueous NaHCO$_3$ solution and an aqueous NaCl solution and then dried over Na$_2$SO$_4$ and concentrated to dryness to obtain 54 g of white powder (Yield: 68%).

(2) Synthesis of BocAsp(OBzl)Ser(Bzl)OBzl

TFA/CH$_2$Cl$_2$=1/1 (200 ml) was added to BocSer(Bzl)OBzl 30 g (78 mmol) and stirred at room temperature for one hour. The mixture was concentrated under reduced pressure to remove TFA and CH$_2$Cl$_2$. The residue was dissolved in ethyl acetate, neutralized with an aqueous NaHCO$_3$ solution, washed with an aqueous NaCl solution, dried over Na$_2$SO$_4$ and evaporated to remove ethyl acetate.

The resulting product and BocAsp(OBzl)OSu 32.8 g (78 mmol) were dissolved in CH$_2$Cl$_2$ 500 ml and stirred overnight. The mixture was evaporated to remove CH$_2$Cl$_2$ and dissolved in ethyl acetate. The product was washed with an aqueous NaHCO$_3$ solution, 1 M citiric acid solution and an aqueous NaCl solution, dried over Na$_2$SO$_4$ and concentrated under reduced pressure to dryness to obtain 41 g of white powder (yield: 89%).

(3) Synthesis of BocGlyAsp(OBzl)Ser(Bzl)OBzl

TFA:CH$_2$Cl$_2$=1:1 (200 ml) was added to BocAsp(OBzl)Ser(Bzl)OBzl 35 g (59 mmol) and the mixture was stirred at room temperature for one hour and then, TFA and CH$_2$Cl2 were concentrated under reduced pressure. The residue was dissolved in ethyl acetate, neutralized with an aqueous NaHCO$_3$ solution and washed with an aqueous NaCl solution. The solution was dried over Na$_2$SO$_4$ and evaporated to remove ethyl acetate.

The resulting product and BocGly 9.8 g (59 mmol) were dissolved in CH$_2$Cl$_2$ to which DCC 12.2 g (59 mmol) was added under ice cooling, stirred for 3 hours and stirred at room temperature overnight. The mixture was filtered to remove DCurea and concentrated under reduced pressure. The residue was dissolved in ethyl acetate and washed with an aqueous NaHCO$_3$ solution, 1 M citric acid solution and an aqueous NaCl solution. The solution was dried over Na$_2$SO$_4$ and evaporated under reduced pressure to obtain white powder 30.5 g (Yield:75%).

(4) Synthesis of BocArg(Mts)GlyAsp(OBzl)Ser(Bzl)OBzl

TFA:CH$_2$Cl$_2$=1:1 (200 ml) was added to BocGlyAsp (OBzl) Ser(Bzl)OBzl (25 g, 39 mmol) and the mixture was stirred at room temperature for one hour and then, TFA and CH$_2$Cl$_2$ were concentrated under reduced pressure. The residue was dissolved in ethyl acetate, neutralized with an aqueous NaHCO$_3$ solution and washed with an aqueous NaCl solution. The solution was dried over Na$_2$SO$_4$ and evaporated to remove ethyl acetate.

The resulting product and BocArg(Mts) 17.8 g (39 mmol) were dissolved in 400 ml of DMF, to which DCC 8.0 g (39 mmol) and HOBt 6.8 g (45 mmol) were added under ice cooling, stirred for 3 hours and stirred at room temperature overnight. The mixture was filtered to remove DCurea and concentrated under reduced pressure. The residue was dissolved in ethyl acetate and washed with an aqueous NaHCO$_3$ solution, 1 M citric acid solution and an aqueous NaCl solution. The solution was dried over Na$_2$SO$_4$ and evaporated under reduced pressure to obtain white powder 19.5 g (Yield:50%).

(5) Synthesis of Synthetic product 15

TFA: CH$_2$Cl$_2$=1:1 (100 ml) was added to BocArg(Mts) GlyAsp(OBzl)Ser(Bzl)OBzl(15.0 g, 15 mmol) and the mixture was stirred at room temperature for one hour and then, TFA and CH$_2$Cl$_2$ were concentrated under reduced pressure. The residue was dissolved in ethyl acetate, neutralized with an aqueous NaHCO$_3$ solution and washed with an aqueous NaCl solution. The solution was dried over Na$_2$SO$_4$ and evaporated to remove ethyl acetate.

The resulting product and carboxyethyl methacrylamide (2.4 g, 15 mmol) were dissolved in 200 ml of CH$_2$Cl$_2$, to which DCC 3.1 g (15 mmol) was added under ice cooling, stirred for 3 hours and stirred at room temperature overnight. The solution was concentrated under reduced pressure. Acetone was added to the residue. The mixture was filtered to remove DCurea precipitated and concentrated under reduced pressure. The residue was washed with ethyl acetate and then ether. The solution was evaporated under reduced pressure to obtain white powder 10.0 g (yield: 65%).

A TFA solution of 1 M trifluoromethanesulfonic acid-thioanisole-m-cresol was added to a TFA solution of the resulting product (10 g, 9.8 mmol) under ice cooling and reacted for one hour to remove the protective groups in the side chains and the terminal ends. The mixture was poured into ether. The oily precipitate was dissolved in distilled water. The solution was washed with ethyl acetate, passed through an anion exchange column (Amberlite IRA-400; Cl type) to convert the target compound to hydrochloride and lyophilized to obtain white powder (4.8 g, yield: 80%).

Amino acid analysis (nmol/50 µl)

R: 0.9877

G 0.9916

D: 0.9899

S: 0.8891

β-alanine 1.0115

Mass spectrum M$^+$: 573

SYNTHETIC EXAMPLE 16

Synthetic product 16

CH$_2$=CCH$_3$—CO—NH—C$_2$H$_4$—CO-RGDSGNH$_2$ (SEQ ID NO:13)

In the same manner as in Synthetic Example 15, the peptide chain was extended as summarized below.

(1) Synthesis of BocSer(Bzl)GlyNH$_2$

BocSer(Bzl) : 59 g (0.2 mol)

GlyNH$_2$.HCl: 22.1 g (0.2 mol)

N-methylmorpholine 20.2 g (0.2 mol)

CH$_2$ Cl$_2$ : 800 ml

DCC 41.2 g (0.2 mol)

Yield of (1): 58.3 g (Yield 83% )

(2) Synthesis of BocAsp(OBzl)Ser(Bzl)GlyNH$_2$

Product of (1): 56.2 g (0.16 mol)

TFA/CH$_2$Cl$_2$: 200 ml/200 ml

BocAsp(OBzl): 51.7 g (0.16 mol)

CH$_2$Cl$_2$ 800 ml

DCC: 33 g (0.16 mol)

Yield of (2): 71.2 g (Yield: 80% )

(3) Synthesis of BocGlyAsp(OBzl)Ser(Bzl)GlyNH$_2$

Product of (2): 66.7 g (0.12 mol)

TFA/CH$_2$Cl$_2$: 200 ml/200 ml

BocGly: 51.7 g (0.12 mol)

CH$_2$Cl$_2$: 700 ml

DCC: 24.7 (0.12 mol)

Yield of (3): 61.8 g (Yield : 84%)

(4) Synthesis of BocArg(Mts)GlyAsp(OBzl)Ser(Bzl) GlyNH$_2$

Product of 839 : 61.3 g (0.1 mol)

TFA/CH$_2$Cl$_2$: 200 ml/200 ml

BocArg(Mts): 45.6 g (0.1 mol)

DMF: 800 ml

DCC: 22.5 (0.1 mol)

HOBt: 14 g (0.1 mol)

Yield of (4): 42.8 g (Yield 45%)

(5) Synthesis of Synthetic product 16

Product of (4) 5.0 g (5.3 mmol)

TFA/CH$_2$Cl$_2$: 50 ml/50 ml

Carboxyethyl methacrylamide: 0.83 g (5.3 mmol)

DMF: 50 ml

DCC: 1.1 g (5.3 mmol)

HOBt: 0.72 g (5.3 mmol)

TFA solution of 1 M trifluoromethanesulfonic acid-thioanisole-m-cresol: 250 ml

Treatment by Amberlite IRA-400; Cl type

Synthetic product 16: 2.29 g (Yield 65%)

Amino acid analysis (nmol/50 µl)

R: 0.9517

G: 2.1004

D: 0.9753

S: 0.8926

β-alanine: 1.0143

Mass spectrum M$^+$: 629

SYNTHETIC EXAMPLE 17

Synthetic product 17

RGDG-NH—C$_2$H$_4$—NH—CO—CCH$_3$=CH$_2$ (SEQ ID NO:14)

Synthetic product 15 was synthesized by a liquid phase method according to a sequential-extension method.

(1) Synthesis of BocGlyONb

BocSer(Bzl) 60 g (0.2 mol) was added to 400 ml of ethyl acetate, to which triethylamine 21 g (0.2 mol) and benzyl bromide 35.4 g (0.2 mol) were added and reacted under refluxing condition for 4 hours. After cooled, the salt produced was separated by filtration. The filtrate was washed with an aqueous $NaHCO_3$ solution and an aqueous NaCl solution and then dried over $Na_2SO_4$ and concentrated to dryness to obtain 54 g of white powder (Yield: 68%).

BocGly 35 g (0.2 mol), triethylamine (28 ml, 0.2 mol) and p-nitrobenzyl bromide (43.2 g, 0.2 mol) were added to 400 ml of ethyl acetate and the mixture was refluxed for 5 hours and left standing overnight at room temperature. The mixture was filtered and the filtrate was washed with an aqueous $NaHCO_3$ solution and water, dried over $Na_2SO_4$ and concentrated under reduced pressure. The resulting procduct was recrystalized from ethyl acetate-hexane. Yield 52.7 g, 85%).

In the same manner as in Synthetic Example 15, the pepetide chain was extended as summarized below.

(2) Synthesis of BocAsp(OBzl)GlyONb
   Product of (1): 46.5 g (0.15 mol)
   $TFA/CH_2Cl_2$: 200 ml/200 ml
   BocAsp(OBzl): 48.5 g (0.15 mol)
   $CH_2Cl_2$: 750 ml
   DCC: 30.9 g (0.15 mol)
   Yield of (2) 64.0 g (Yield : 80%)

(3) Synthesis of BocGlyAsp(OBzl)GlyONb
   Product of (2): 64.0 g (0.12 mol)
   $TFA/CH_2Cl_2$: 200 ml/200 ml
   BocGly: 21 g (0.12 mol)
   $CH_2Cl_2$: 750 ml
   DCC: 24.7 g (0.12 mol)
   Yield of (3): 58.8 g (Yield: 83%)

(4) Synthesis of BocArg(Mts)GlyAsp(OBzl)GlyONb
   Product of (3): 53.7 g (91 mmol)
   $TFA/CH_2Cl_2$: 200 ml/200 ml
   BocArg(Mts): 41.5 g (91 mmol)
   DMF: 800 ml
   DCC: 18.7 g (91 mmol)
   HOBt: 13.5 g (0.1 mol)
   Yield of (4): 46.5 g (Yield: 55%)

(5) Synthesis of BocArg(Mts)GlyAsp(OBzl)Gly

The product of (4) (9.29 g, 10 mmol) was dissolved in 300 ml of 90% acetic acid, to which 32.7 g (0.5 mol) of Zn powder was added and stirred at 0° C. for 3 hours. The Zn powder was filtered and the filtrate was concentrated under reduced pressure. Citric acid was added to make the solution acidic and the solution was extracted with ethyl acetate. The extracted solution was dried over $Na_2SO_4$ and concentrated under reduced pressure. Ether was added to the residue to obtain white powder (6.26 g, yield: 79%).

(6) Synthesis of Synthetic product 17
   Product of (5): 5.31 g (6.7 mmol)
   Aminoethyl methacrylamide: 0.86 g (6.7 mmol)
   DMF: 60 ml
   DCC: 1.4 g (6.7 mmol)
   HOBt: 0.95 g (7 mmol)
   TFA solution of 1 M trifluoromethanesulfonic acid-thioanisole-m-cresol: 250 ml
   Treatment by Amberlite IRA-400; Cl type
   Synthetic product 17: 2.9 g (Yield: 75%)
   Amino acid analysis (nmol/50 µl)
   R: 4.5915
   G: 9.4324
   D: 4.6618
   Mass spectrum $M^+$: 514

SYNTHETIC EXAMPLE 18

Synthetic product 18
   $CH_2$=$CCH_3$—CO—NH—$C_2H_4$—CO-RGDG-NH—$C_2H_4$—NH—CO—$CCH_3$=$CH_2$ (SEQ ID NO:15)

The same procedures as in (1) to (5) of Synthetic Example 17 and the following procedures were conducted to obtain Synthetic product 18.

(1) BocArg(Mts)GlyAsp(OBzl)Gly-NH—$C_2H_4$—NH—CO—$CCH_3$=$CH_2$
   BocArg(Mts)GlyAsp(OBzl)Gly: 5.19 g (6.7 mmol)
   Aminoethyl methacrylamide 0.86 g (6.7 mmol)
   DMF: 60 ml
   DCC: 1.4 g (6.7 mmol)
   HOBt: 0.95 g (7 mmol)
   Yield of (1) 4.7 g (Yield: 80 %)
   Mass spectrum $M^+$: 885

(2) Synthesis of Synthetic product 18
   Product of (1): 4.4 g (5 mmol)
   $TFA/CH_2Cl_2$: 50 ml/50 ml
   Carboxyethyl methacrylamide: 0.79 g (5 mmol)
   DMF: 50 ml
   DCC: 1.03 g (5 mmol)
   HOBt: 0.68 g (5 mmol)
   TFA solution of 1 M trifluoromethanesulfonic acid-thioanisole-m-cresol: 250 ml
   Treatment by Amberlite IRA-400; Cl type
   Synthetic product 18: 2.41 g (Yield: 70%)
   Amino acid analysis (nmol/50 µl)
   R: 8.8963
   G: 17.9746
   D: 8.7531
   β-alanine: 8.8330
   Mass spectrum $M^+$: 653

SYNTHETIC EXAMPLE 19

Synthetic product 15 was polymerized by radical polymerization.

Synthetic product 15 (500 mg) was dissolved in 5 ml of water and adjusted to pH 7.4 with 1 N NaOH. An initiator, potassium persulfate (2.5 mg) and sodium hydrogen sulfite (1.0 mg) were added and polymerization was conducted at 20° C. for 20 hours under nitrogen atmosphere. The polymer was precipitated by ethyl acetate and dialyzed through Spectra/por 7 (fractional molecular weight: 3,000) (available from Spectrum Medical Industries, Inc.) against pure water to remove low molecular fractions followed by lyophilization to obtain Synthetic product 19 (yield: 240 mg).

Synthetic product 19 was subjected to molecular weight fractionation by gel chromatography. Molecular weight was determined in the same method as in Preparation Example 12.
Fraction 1 M.W.: about 48,000 (Synthetic product 19-1)
Fraction 2 M.W.: about 21,000 (synthetic product 19-2)
Fraction 3 M.W.: about 12,000 (Synthetic product 19-3)

SYNTHETIC EXAMPLE 20

Synthetic product 15 alas polymerized in the same manner as in Synthetic Example 19 except that an amount of the initiator was changed as follows.
   Initiator: 10 mg of potassium persulfate
   4 mg of sodium hydrogen sulfite
   Yield: 180 mg (Synthetic product 20)
   M.W.: 5,000

SYNTHETIC EXAMPLES 21 TO 36

Synthetic products 1 to 14, 16 and 17 were polymerized in the same manner as in Synthetic Example 19. The results are shown in the following table.

| Synthetic Example (Synthetic product No.) | Monomer | Yield of polymer (mg) | Molecular weight |
| --- | --- | --- | --- |
| 21 | Synthetic product 1 | 230 | 15000 |
| 22 | Synthetic product 2 | 180 | 13000 |
| 23 | Synthetic product 3 | 190 | 15000 |
| 24 | Synthetic product 4 | 150 | 11000 |
| 25 | Synthetic product 5 | 240 | 16000 |
| 26 | Synthetic product 6 | 120 | 8000 |
| 27 | Synthetic product 7 | 170 | 10000 |
| 28 | Synthetic product 8 | 140 | 9000 |
| 29 | Synthetic product 9 | 170 | 11000 |
| 30 | Synthetic product 10 | 130 | 12000 |
| 31 | Synthetic product 11 | 150 | 9000 |
| 32 | Synthetic product 12 | 140 | 8000 |
| 33 | Synthetic product 13 | 130 | 8000 |
| 34 | Synthetic product 14 | 170 | 10000 |
| 35 | Synthetic product 15 | 200 | 15000 |
| 36 | Synthetic product 17 | 190 | 13000 |

For Synthetic product 8, water/methanol (1/1) was used as a solvent for the polymerization and for the dialysis.

SYNTHETIC EXAMPLE 37

Synthetic product 18 prepared in Synthetic Example 18 was polymerized by radical polymerization to obtain a hydrogel.

A pair of silane treated glass plates (5 cm×6 cm×1 cm) and a gasket were provided. Synthetic product 15 (2 g, 3.2 mmol) and Synthetic product 18 (0.21 g, 0.3 mmol) were dissolved in 12 ml of distilled water and adjusted to pH 7.4 by 1 N NaOH. Ammonium persulfate (11 mg) was added and a nitrogen gas was supplied through the mixture to remove air therein. The mixture was injected between the glass plates which were then vised. Polymerization was conducted at 60° C. for 40 hours. A hydrogel produced was washed with distilled water to remove unreacted monomer. The gel (Synthetic product 37) was sterilized by an ultraviolet lamp before it was used for cultivating animal cells.

SYNTHETIC EXAMPLE 38

Synthetic product 15 and the monomer (677 mg, 3.28 mmol) prepared in Preparation Example 1 were copolymerized by radical polymerization.

Synthetic product 15 (500 mg, 0.82 mmol) and the monomer (677 mg, 3.28 mmol) prepared in Preparation Example 1 were dissolved in 10 ml of water and adjusted to pH 7.4 with 1 N NaOH. An initiator, potassium persulfate (5.1 mg) and sodium hydrogen sulfite (2.0 mg) were added and polymerization was conducted at 20° C. for 20 hours under nitrogen atmosphere. The polymer was precipitated by ethyl acetate and dialyzed through Spectra/por 7 (fractional molecular weight: 3,000) against pure water to remove low molecular fractions followed by lyophilization to obtain Synthetic product 38 (yield: 490 mg).

Amino acid analysis of the copolymer showed that Synthetic product 15 was introduced in the copolymer in an amount of 19% (which was calculated from the values for β-alanine and Gly). Amino acid analysis (nmol/50 μl)

R: 4.0835
G: 4.2832
D: 4.1692
S: 3.9211
β-alanine 22.1927

Synthetic product 38 was subjected to molecular weight fractionation by gel chromatography. Molecular weight was determined in the same method as in Preparation Example 12.

Fraction 1 M.W.: about 53,000 (Synthetic product 38-1)

Fraction 2 M.W.: about 21,000 (Synthetic product 38-2)

Fraction 3 M.W.: about 8,000 (Synthetic product 38-3)

SYNTHETIC EXAMPLE 39

Synthetic product 15 and the monomer prepared in Preparation Example 1 were copolymerized in the same manner as in SYNTHETIC EXAMPLE 38 except that an amount of the initiator was changed as follows.

Initiator: 20.3 mg of potassium persulfate 8.1 mg of sodium hydrogen sulfite
Yield: 315 mg (Synthetic product 39)
M.W.: 4,000
The amount of Synthetic product 15 introduced (calculated from the values for β-alanine and Gly): 19%
Amino acid analysis (nmol/50 μl)
R: 5.8235
G: 6.0821
D: 5.9632
S: 5.3185
β-alanine: 30.4105

SYNTHETIC EXAMPLES 40 AND 41

Copolymerization was conducted in the same manner as in Synthetic Example 19 except that a monomer composition was changed.

SYNTHETIC EXAMPLE 21

Monomer Synthetic product 15 500 mg (0.82 mmol)

Preparation product 1 129 mg (0.82 mmol)
Initiator Potassium persulfate 3.1 mg
Sodium hydrogen sulfite 1.3 mg
Yield 273 mg (Synthetic product 21)
M.W. 18000
The amount of Synthetic product 15 introduced (calculated from the values for β-alanine and Gly): 48%

Amino acid analysis (nmol/50 μl)
R: 6.2135
G: 6.5521
D: 6.3896
S: 5.9892
β-alanine: 13.7939

SYNTHETIC EXAMPLE 22

Monomer Synthetic product 15 500 mg (0.82 mmol)
Preparation product 1 2.45 g (15.58 mmol)
Initiator Potassium persulfate 14.8 mg
Sodium hydrogen sulfite 5.9 mg
Yield 1.62 g (Synthetic product 41)
M.W. 42000
The amount of Synthetic product 15 introduced (calculated from the values for β-alanine and Gly): 4%
Amino acid analysis (nmol/50 μl)
R: 0.9631
G: 1.0878
D: 0.9821
S: 0.8922
β-alanine: 28.6251

SYNTHETIC EXAMPLES 42 TO 57

Synthetic products 1 to 14, 16 and 17 were copolymerized with various anionic monomers in the same manner as in Synthetic Example 19.

SYNTHETIC EXAMPLE 42

Monomer Synthetic product 1 500 mg (0.96 mmol)
Preparation product 11 601 mg (3.83 mmol)
Initiator Potassium persulfate 5.6 mg
Sodium hydrogen sulfite 2.2 mg
Yield 513 mg (Synthetic product 42)
M.W. 16000
The amount of Synthetic product 1 introduced (calculated from the values for β-alanine and Gly): 17%
Amino acid analysis (nmol/50 μl)
R: 3.0916
G: 3.2654
D: 3.1262
4Abu: 18.8751

SYNTHETIC EXAMPLE 43

Monomer Synthetic product 2 500 mg (0.56 mmol)
Preparation product 9 323 mg (3.83 mmol)
Initiator Potassium persulfate 8.2 mg
Sodium hydrogen sulfite 3.3 mg
Yield 495 mg (Synthetic product 43)
M.W. 17,000
The amount of Synthetic product 2 introduced (calculated from the values for β-alanine and Gly): 21%
Amino acid analysis (nmol/50 μl)
R: 2.6911
G: 8.1692
D: 2.7816
β-alanine: 1.4023

SYNTHETIC EXAMPLE 44

Monomer Synthetic product 3 500 mg (0.4 mmol)
Acrylamidoglycolic acid 232 mg (1.6 mmol) (available from Aldrich)
Initiator Potassium persulfate 3.7 mg
Sodium hydrogen sulfite 1.5 mg
Yield 324 mg (Synthetic product 44)
M.W. 9,000
The amount of Synthetic product 3 introduced (calculated from the N value of the elemental analysis): 19% N value of the elemental analysis: 17.43%

SYNTHETIC EXAMPLE 45

Monomer Synthetic product 4 500 mg (0.25 mmol)
Preparation product 9 143 mg (1.0 mmol)
Initiator Potassium persulfate 3.2 mg
Sodium hydrogen sulfite 1.3 mg
Yield 232 mg (Synthetic product 45)
M.W. 11,000
The amount of Synthetic product 4 introduced (calculated from the values for β-alanine and Gly): 16%
Amino acid analysis (nmol/50 μl)
R: 4.7623
G: 24.9472
D: 4.8513
β-alanine: 2.4615

SYNTHETIC EXAMPLE 46

Monomer Synthetic product 5 500 mg (0.82 mmol)
Itaconic acid 429 mg (3.28 mmol)
Initiator Potassium persulfate 4.6 mg
Sodium hydrogen sulfite 1.9 mg
Yield 372 mg (Synthetic product 46)
M.W. 16,000
The amount of Synthetic product 5 introduced (calculated from the N value of the elemental analysis): 24%
N value of the elemental analysis: 10.98%

SYNTHETIC EXAMPLE 47

Monomer Synthetic product 6 500 mg (0.77 mmol)
Preparation product 10 667 mg (3.08 mmol)
Initiator Potassium persulfate 5.8 mg
Sodium hydrogen sulfite 2.3 mg
Yield 427 mg (Synthetic product 47)
M.W. 12,000
The amount of Synthetic product 6 introduced (calculated from the values for Glu and Gly): 19%
Amino acid analysis (nmol/50 μl)
R: 2.9158
G: 3.2965
D: 3.1106
S: 2.8765
Glutamic acid: 14.0535

SYNTHETIC EXAMPLE 48

Monomer Synthetic product 7 500 mg (0.77 mmol)
Methacrylic acid 267 mg (3.08 mmol) (available from Tokyo Kasei)
Initiator Potassium persulfate 3.8 mg
Sodium hydrogen sulfite 1.5 mg
Yield 287 mg (Synthetic product 48)
M.W. 90,000
The amount of Synthetic product 7 introduced (calculated from the N value of the elemental analysis): 17%
N value of the elemental analysis: 10.46%

SYNTHETIC EXAMPLE 49

Monomer Synthetic product 8 500 mg (0.69 mmol)
Acrylic acid 202 mg (2.76 mmol) (available from Tokyo Kasei)
Initiator Potassium persulfate 3.5 mg
Sodium hydrogen sulfite 1.4 mg
Yield 233 mg (Synthetic product 49)
M.W. 10,000
The amount of Synthetic product 8 introduced (calculated from the N value of the elemental analysis): 14%
N value of the elemental analysis: 9.62%
Water/methanol (1/1) was used as a polymerization solvent and a dialysis solvent.

SYNTHETIC EXAMPLE 50

Monomer Synthetic product 9 500 mg (0.79 mmol)
Preparation product 1 487 mg (3.16 mmol)
Initiator Potassium persulfate 4.9 mg
Sodium hydrogen sulfite 2.0 mg
Yield 411 mg (Synthetic product 50)
M.W. 12,000
The amount of Synthetic product 9 introduced (calculated from the values for β-alanine and Gly): 18%
Amino acid analysis (nmol/50 μl)
R: 4.2569
G: 4.3812
D: 4.2115
S: 3.9364
β-alanine: 20.0948
  leucine: 4.0255

SYNTHETIC EXAMPLE 51

Monomer Synthetic product 10 500 mg (0.75 mmol)
Preparation product 9 429 mg (3.0 mmol)
Initiator Potassium persulfate 4.6 mg
Sodium hydrogen sulfite 1.9 mg
Yield 362 mg (Synthetic product 51)
M.W. 14,000
The amount of Synthetic product 10 introduced (calculated from the values for Glu and Asp): 17%
Amino acid analysis (nmol/50 μl)
R: 3.7622
G: 22.8479
D: 3.8613
S: 3.5926
Glutamic acid: 3.7239

SYNTHETIC EXAMPLE 52

Monomer Synthetic product 11 500 mg (0.79 mmol)
Preparation product 9 458 mg (3.16 mmol)
Initiator Potassium persulfate 4.8 mg
Sodium hydrogen sulfite 1.9 mg
Yield 362 mg (Synthetic product 52)
M.W. 13,000
The amount of Synthetic product 10 introduced (calculated from the values for Asp and Gly): 20%
Amino acid analysis (nmol/50 μl)
R: 4.6511
G: 23.7362
D: 4.7235
S: 4.4052

SYNTHETIC EXAMPLE 53

Monomer Synthetic product 12 500 mg (0.71 mmol)
Preparation product 1 440 mg (2.84 mmol)
Initiator Potassium persulfate 4.7 mg
Sodium hydrogen sulfite 1.9 mg
Yield 395 mg (Synthetic product 53)
M.W. 15,000
The amount of Synthetic product 12 introduced (calculated from the values for β-alanine and Gly): 17%
Amino acid analysis (nmol/50 μl)
R: 2.9615
G: 6.3044
D: 3.0888
S: 2.7812
β-alanine: 12.1295

SYNTHETIC EXAMPLE 54

Monomer Synthetic product 13 500 mg (0.72 mmol)
Preparation product 1 455 mg (2.88 mmol)
Initiator Potassium persulfate 4.8 mg
Sodium hydrogen sulfite 1.9 mg
Yield 343 mg (Synthetic product 54)
M.W. 13,000
The amount of Synthetic product 13 introduced (calculated from the values for β-alanine and Gly): 20%
Amino acid analysis (nmol/50 μl)
R: 3.2611
G: 6.8312
D: 3.3626
S: 3.0022
P: 3.1263
β-alanine: 10.2468

SYNTHETIC EXAMPLE 55

Monomer Synthetic product 14 500 mg (0.72 mmol)
Preparation product 2 455 mg (2.88 mmol)
Initiator Potassium persulfate 4.8 mg
Sodium hydrogen sulfite 1.9 mg
Yield 401 mg (Synthetic product 55)
M.W. 11,000
The amount of Synthetic product 14 introduced (calculated from the values for 4Abu and Gly): 22%
Amino acid analysis (nmol/50 μl)
R: 2.5536
G: 10.8612
D: 2.6211
S: 2.3628
4Abu: 9.7976

SYNTHETIC EXAMPLE 56

Monomer Synthetic product 16 500 mg (0.75 mmol)
Preparation product 1 471 mg (3.00 mmol)
Initiator Potassium persulfate 4.9 mg
Sodium hydrogen sulfite 1.9 mg
Yield 388 mg (Synthetic product 56)
M.W. 15,000
The amount of Synthetic product 16 introduced (calculated from the values for β-alanine and Gly): 19%
Amino acid analysis (nmol/50 μl)
R: 3.5287
G: 7.5128

D: 3.6633
S: 3.3151
β-alanine: 23.8441

SYNTHETIC EXAMPLE 57

Monomer Synthetic product 17 500 mg (0.85 mmol)
Preparation product 1 534 mg (3.40 mmol)
Initiator Potassium persulfate 5.2 mg
Sodium hydrogen sulfite 2.1 mg
Yield 341 mg (Synthetic product 57)
M.W. 11,000
The amount of Synthetic product 17 introduced (calculated from the values for β-alanine and Gly): 16%
Amino acid analysis (nmol/50 μl)
R: 4.5531
G: 9.3384
D: 4.5938
β-alanine: 24.5133

SYNTHETIC EXAMPLE 58

Synthetic products 15 and 18 was copolymerized with Preparation product 1 by radical polymerization to obtain a hydrogel.

A pair of silane treated glass plates (5 cm×6 cm×1 cm) and a gasket were provided. Synthetic product 15 (0.23 g, 0.4 mmol), Synthetic product 18 (0.28 g, 0.4 mmol) and Preparation product 1 (1.49 g, 9.4 mmol) were dissolved in distilled water to obtain a 10 wt % monomer solution which was then adjusted to pH 7.4 by 1 N NaOH. Ammonium persulfate (10.4 mg) was added and a nitrogen gas was supplied through the mixture to remove air therein. The mixture was injected between the glass plates which were then vised. Polymerization was conducted at 60° C. for 40 hours. A hydrogel produced was washed with distilled water to remove unreacted monomers. The amount of the monomer (Synthetic products 15 and 18) introduced in Synthetic product 58 was about 8% calculated from the N value (12.07%) of the elemental analysis. The gel (Synthetic product 58) was sterilized by an ultraviolet lamp before it was used for cultivating animal cells.

SYNTHETIC EXAMPLE 59

Synthetic product 15 was copolymerized with Preparation product 14 by radical polymerization.

Synthetic product 15 (500 mg, 0.82 mmol) and the monomer prepared in Preparation Example 14 (677 mg, 3.3 mmol) were dissolved in 10 ml of water and adjusted to pH 7.4 with 1 N NaOH. An initiator, potassium persulfate (6.0 mg) and sodium hydrogen sulfite (2.4 mg) were added and polymerization was conducted at 20° C. for 20 hours under nitrogen atmosphere. The polymer was precipitated by ethyl acetate and dialyzed through Spectra/por 7 (fractional molecular weight: 3,000) against pure water to remove low molecular fractions followed by lyophilization to obtain Synthetic product 59 (yield: 243 mg).

The amount of Synthetic product 15 introduced in the copolymer 59 was found 18% from the N value of the elemental analysis.

Synthetic product 59 was subjected to molecular weight fractionation by gel chromatography. Molecular weight was determined in the same method as in Preparation Example 16.

Fraction 1 M.W.: about 50,000 (Synthetic product 59-1)
Fraction 2 M.W.: about 23,000 (Synthetic product 59-2)
Fraction 3 M.W.: about 11,000 (Synthetic product 59-3)

SYNTHETIC EXAMPLE 60

Synthetic product 15 was copolymerized with Preparation product 14 in the same manner as in Synthetic Example 59 except that an amount of the initiator was changed as follows.

Initiator: 23.8 mg of potassium persulfate
9.4 mg of sodium hydrogen sulfite
Yield: 165 mg (Synthetic product 60)
M.W.: 4,500
The amount of Synthetic product 15 introduced: 19%
N value of the elemental analysis: 15.54%

SYNTHETIC EXAMPLES 61 AND 62

Copolymerization was conducted in the same manner as in Synthetic Example 59 except that a monomer composition was changed.

SYNTHETIC EXAMPLE 61

Monomer Synthetic product 15 500 mg (0.82 mmol)
Preparation product 14 169 mg (0.82 mmol)
Initiator Potassium persulfate 3.3 mg
Sodium hydrogen sulfite 1.3 mg
Yield 134 mg (Synthetic product 61)
M.W. 15,000
The amount of Synthetic product 15 introduced: 45%
N value of the elemental analysis: 16.99%

SYNTHETIC EXAMPLE 62

Monomer Synthetic product 15 500 mg (0.82 mmol)
Preparation product 14 322 mg (15.58 mmol)
Initiator Potassium persulfate 18.6 mg
Sodium hydrogen sulfite 7.5 mg
Yield 1.52 g (Synthetic product 62)
M.W. 35,000
The amount of Synthetic product 15 introduced: 4%
N value of the elemental analysis: 14.09%

SYNTHETIC EXAMPLES 63 TO 78

Synthetic products 1 to 14, 16 and 17 were copolymerized with various cationic monomers in the same manner as in Synthetic Example 59.

SYNTHETIC EXAMPLE 62

Monomer Synthetic product 1 500 mg (0.96 mmol)
Preparation product 15 1370 mg (3.83 mmol)
Initiator Potassium persulfate 9.4 mg
Sodium hydrogen sulfite 3.8 mg
Yield 564 mg (Synthetic product 63)
M.W. 9,000
The amount of Synthetic product 1 introduced (calculated from the values for Arg/Gly): 22%
Amino acid analysis (nmol/50 μl)
R: 29.8842
G: 6.4251
D: 6.1233

SYNTHETIC EXAMPLE 64

Monomer Synthetic product 2 500 mg (0.56 mmol)
Chlorotrimethylammoniopropyl methacrylamide (available from Aldrich) 498 mg (2.26 mmol)
Initiator Potassium persulfate 5.0 mg
Sodium hydrogen sulfite 2.0 mg
Yield 320 mg (Synthetic product 64)
M.W. 12,000
The amount of Synthetic product 2 introduced (calculated from the N value of the elemental analysis): 19%
N value of the elemental analysis: 16.50%

SYNTHETIC EXAMPLE 65

Monomer Synthetic product 3 500 mg (0.40 mmol)
Chlorotrimethylammoniopropyl methacrylamide (available from Aldrich) 353 mg (1.60 mmol)
Initiator Potassium persulfate 4.3 mg
Sodium hydrogen sulfite 1.7 mg
Yield 262 mg (Synthetic product 65)
M.W. 13,000
The amount of Synthetic product 3 introduced (calculated from the N value of the elemental analysis): 18%
N value of the elemental analysis: 17.45%

SYNTHETIC EXAMPLE 66

Monomer Synthetic product 4 500 mg (0.25 mmol)
Dimethylaminoethyl methacrylate (available from Aldrich) 144 mg (1.00 mmol)
Initiator Potassium persulfate 3.2 mg
Sodium hydrogen sulfite 1.3 mg
Yield 186 mg (Synthetic product 66)
M.W. 10,000
The amount of Synthetic product 4 introduced (calculated from the N value of the elemental analysis): 23%
N value of the elemental analysis: 19.56%

SYNTHETIC EXAMPLE 67

Monomer Synthetic product 5 500 mg (0.82 mmol)
Preparation product 15 1170 mg (3.28 mmol)
Initiator Potassium persulfate 8.4 mg
Sodium hydrogen sulfite 3.4 mg
Yield 415 mg (Synthetic product 67)
M.W. 8,000
The amount of Synthetic product 5 introduced (calculated from the values for Arg and Gly): 20%
Amino acid analysis (nmol/50 µl)
R: 16.8129
G: 3.4252
D: 3.3812
S: 3.0216
β-alanine: 3.3846

SYNTHETIC EXAMPLE 68

Monomer Synthetic product 6 500 mg (0.77 mmol)
Dimethylaminoethyl acrylate (available from Aldrich) 440 mg (3.08 mmol)
Initiator Potassium persulfate 4.7 mg
Sodium hydrogen sulfite 1.9 mg
Yield 353 mg (Synthetic product 68)
M.W. 9,000
The amount of Synthetic product 6 introduced (calculated from the N value of the elemental analysis): 21%
N value of the elemental analysis: 13.86%

SYNTHETIC EXAMPLE 69

Monomer Synthetic product 7 500 mg (0.77 mmol)
Preparation product 14 635 mg (3.08 mmol)
Initiator Potassium persulfate 3.2 mg
Sodium hydrogen sulfite 1.3 mg
Yield 183 mg (Synthetic product 69)
M.W. 12,000
The amount of Synthetic product 7 introduced (calculated from the N value of the elemental analysis): 24%
N value of the elemental analysis: 15.38%

SYNTHETIC EXAMPLE 70

Monomer Synthetic product 8 500 mg (0.69 mmol)
Dimethylaminoethyl acrylate 396 mg (2.76 mmol)
Initiator Potassium persulfate 4.5 mg
Sodium hydrogen sulfite 1.8 mg
Yield 215 mg (Synthetic product 70)
M.W. 8,000
The amount of Synthetic product 8 introduced (calculated from the N value of the elemental analysis): 21%
N value of the elemental analysis: 13.07%
Water/methanol (1/1) was used as a polymerization solvent and a dialysis solvent.

SYNTHETIC EXAMPLE 71

Monomer Synthetic product 9 500 mg (0.79 mmol)
Preparation product 14 430 mg (3.16 mmol)
Initiator Potassium persulfate 5.7 mg
Sodium hydrogen sulfite 2.3 mg
Yield 284 mg (Synthetic product 71)
M.W. 9,000
The amount of Synthetic product 9 introduced (calculated from the N value of the elemental analysis): 17%
N value of the elemental analysis: 15.12%

SYNTHETIC EXAMPLE 72

Monomer Synthetic product 10 500 mg (0.75 mmol)
Dimethylaminoethyl acrylate 430 mg (3.0 mmol)
Initiator Potassium persulfate 4.2 mg
Sodium hydrogen sulfite 1.7 mg
Yield 176 mg (Synthetic product 72)
M.W. 8,000
The amount of Synthetic product 10 introduced (calculated from the N value of the elemental analysis): 17%
N value of the elemental analysis: 14.26%

SYNTHETIC EXAMPLE 73

Monomer Synthetic product 11 500 mg (0.79 mmol)
Preparation product 15 1132 mg (3.16 mmol)
Initiator Potassium persulfate 8.2 mg
Sodium hydrogen sulfite 3.3 mg
Yield 510 mg (Synthetic product 73)
M.W. 12,000
The amount of Synthetic product 11 introduced (calculated from the values for Arg and Gly): 18%
Amino acid analysis (nmol/50 µl)
R: 17.8246
G: 3.2619

D: 3.0611
S: 2.8926

SYNTHETIC EXAMPLE 74

Monomer Synthetic product 12 500 mg (0.71 mmol)
Preparation product 14 584 mg (2.84 mmol)
Initiator Potassium persulfate 5.4 mg
Sodium hydrogen sulfite 2.2 mg
Yield 265 mg (Synthetic product 74)
M.W. 10,000
The amount of Synthetic product 12 introduced (calculated from the N value of the elemental analysis): 20%
N value of the elemental analysis: 15.52%

SYNTHETIC EXAMPLE 75

Monomer Synthetic product 13 500 mg (0.72 mmol)
Chlorotrimethylammoniopropyl methacrylamide 638 mg (2.88 mmol)
Initiator Potassium persulfate 5.7 mg
Sodium hydrogen sulfite 2.3 mg
Yield 322 mg (Synthetic product 75)
M.W. 13,000
The amount of Synthetic product 13 introduced (calculated from the N value of the elemental analysis): 22%
N value of the elemental analysis: 15.28%

SYNTHETIC EXAMPLE 76

Monomer Synthetic product 14 500 mg (0.72 mmol)
Chlorotrimethylammoniopropyl methacrylamide 638 mg (2.88 mmol)
Initiator Potassium persulfate 5.7 mg
Sodium hydrogen sulfite 2.3 mg
Yield 361 mg (Synthetic product 76)
M.W. 11,000
The amount of Synthetic product 14 introduced (calculated from the N value of the elemental analysis): 20%
N value of the elemental analysis: 16.69%

SYNTHETIC EXAMPLE 77

Monomer Synthetic product 16 500 mg (0.75 mmol)
Preparation product 14 621 mg (3.00 mmol)
Initiator Potassium persulfate 5.6 mg
Sodium hydrogen sulfite 2.2 mg
Yield 330 mg (Synthetic product 77)
M.W. 13,000
The amount of Synthetic product 16 introduced (calculated from the N value of the elemental analysis): 19%
N value of the elemental analysis: 16.79%

SYNTHETIC EXAMPLE 78

Monomer Synthetic product 17 500 mg (0.85 mmol)
Preparation product 14 702 mg (3.40 mmol)
Initiator Potassium persulfate 6.0 mg
Sodium hydrogen sulfite 2.4 mg
Yield 326 mg (Synthetic product 78)
M.W. 9,000
The amount of Synthetic product 17 introduced (calculated from the N value of the elemental analysis): 20%
N value of the elemental analysis: 16.87%

SYNTHETIC EXAMPLE 79

Synthetic products 15 and 18 was copolymerized with Preparation product 14 by radical polymerization to obtain a hydrogel.

A pair of silane treated glass plates (5 cm×6 cm×1 cm) and a gasket were provided. Synthetic product 15 (0.23 g, 0.4 mmol), Synthetic product 18 (0.28 g, 0.4 mmol) and Preparation product 14 (1.49 g, 7.2 mmol) were dissolved in distilled water to obtain a 10 wt % monomer solution which was then adjusted to pH 7.4 by 1 N NaOH. Ammonium persulfate (11 mg) was added and a nitrogen gas was supplied through the mixture to remove air therein. The mixture was injected between the glass plates which were then vised. Polymerization was conducted at 60° C. for 40 hours. A hydrogel produced was washed with distilled water to remove unreacted monomers. The amount of the monomer (Synthetic products 15 and 18) introduced in Synthetic product 79 was about 12% calculated from the N value (15.68%) of the elemental analysis. The gel (Synthetic product 79) was sterilized by an ultraviolet lamp before it was used for cultivating animal cells.

TEST EXAMPLE 1

Determination of Cell Adhesion-Inhibitory Activity

The propenamide derivatives, the polymers thereof, the copolymers thereof and salts thereof of the present invention have the activity for inhibiting adhesion of cells to fibronectin or vitronectin. A method for determining the activity will be described below. The competitive assays used herein have widely been employed in the field of biochemistry and are detailed in, for instance, "Method in Enzymology", 1981, 82, pp. 803–831; and J.P. KOKAI Nos. Hei 1-309682 and Hei 2-174797.

Experimental Method

1. Preparation of Fibronectin or vitronectin Adsorbed Plate

Commercially available fibronectin (derived from human; purchased from Seikagaku Kogyo K.K.) and vitronectin (derived from human; purchased from Funakoshi Pharmaceuticals) each was diluted to 1.0 μl/ml and 2.0 μl/ml with PBS (NaH$_2$PO$_4$ 0.005 M+NaCl 0.07 M), 0.5 ml of the resulting diluted solution was dispensed into a plastic plate having 24 wells and incubated at 37° C. overnight to perform coating of the plate. Then bovine serum albumin (BSA 1%) was added followed by incubation at 37° C. for one hour for inhibiting the occurrence of nonspecific adsorption, then washing with PBS in the usual manner and sufficient drainage to obtsin a fibronectin or vitronectin adsorbed plate.

2. Adhesion-Inhibitory Test

The propenamide derivatives, the polymers thereof, the copolymers thereof or salts thereof obtained through lyophilization were diluted with Dulbecco's Modified Eagles Medium (hereunder referred to as "DMEM") to obtain solutions of the compounds having concentrations of 0, 0.25, 0.5, 1.0 and 1.5 mg/ml, respectively. Each of the solutions (0.25 ml) was dispensed to the plate prepared above, 0.25 ml of a suspension of endothelium cells of blood vessel (4×10$^6$ cells/ml)was added to the plate and incubated at 37° C. for one hour to thus cause the adhesion of the cells. The plate was washed three times with DMEM medium to remove non-adhered cells, then the adhered cells were peeled off with a 0.025% EDTA trypsin solution and stained with a 2% Trypan Blue solution to count the number of the adhered cells. The results thus obtained are summarized in the following Tables 1 and 2.

TABLE 1

Cell Adhesion-Inhibitory effect Against Fibronectin (cells/well)

| Compound Added | Concentration (mg/ml) | | | | |
|---|---|---|---|---|---|
| | 0 | 0.25 | 0.5 | 1.0 | 1.5 |
| Synthetic product 19-1 | C | B | A | A | A |
| Synthetic product 19-2 | C | B | A | A | A |
| Synthetic product 19-3 | C | B | A | A | A |
| Synthetic product 20 | C | B | A | A | A |
| Synthetic product 21 | C | C | B | B | A |
| Synthetic product 22 | C | B | A | A | A |
| Synthetic product 23 | C | B | A | A | A |
| Synthetic product 24 | C | B | A | A | A |
| Synthetic product 25 | C | B | A | A | A |
| Synthetic product 26 | C | B | A | A | A |
| Synthetic product 27 | C | B | A | A | A |
| Synthetic product 28 | C | B | B | A | A |
| Synthetic product 29 | C | B | A | A | A |
| Synthetic product 30 | C | B | A | A | A |
| Synthetic product 31 | C | B | B | A | A |
| Synthetic product 32 | C | B | A | A | A |
| Synthetic product 33 | C | B | A | A | A |
| Synthetic product 34 | C | B | A | A | A |
| Synthetic product 35 | C | B | A | A | A |
| Synthetic product 36 | C | B | B | A | A |
| Synthetic product 38-1 | C | B | A | A | A |
| Synthetic product 38-2 | C | B | A | A | A |
| Synthetic product 38-3 | C | B | A | A | A |
| Synthetic product 39 | C | B | A | A | A |
| Synthetic product 40 | C | B | A | A | A |
| Synthetic product 41 | C | B | B | B | A |
| Synthetic product 42 | C | C | B | B | A |
| Synthetic product 43 | C | B | A | A | A |
| Synthetic product 44 | C | B | A | A | A |
| Synthetic product 45 | C | B | A | A | A |
| Synthetic product 46 | C | B | A | A | A |
| Synthetic product 47 | C | B | B | A | A |
| Synthetic product 48 | C | B | A | A | A |
| Synthetic product 49 | C | B | B | A | A |
| Synthetic product 50 | C | B | B | A | A |
| Synthetic product 51 | C | B | A | A | A |
| Synthetic product 52 | C | B | A | A | A |
| Synthetic product 53 | C | B | A | A | A |
| Synthetic product 54 | C | B | A | A | A |
| Synthetic product 55 | C | B | A | A | A |
| Synthetic product 56 | C | B | A | A | A |
| Synthetic product 57 | C | B | A | A | A |
| Synthetic product 59-1 | C | B | A | A | A |
| Synthetic product 59-2 | C | B | A | A | A |
| Synthetic product 59-3 | C | B | A | A | A |
| Synthetic product 60 | C | B | A | A | A |
| Synthetic product 61 | C | B | A | A | A |
| Synthetic product 62 | C | C | B | B | A |
| Synthetic product 63 | C | C | B | B | A |
| Synthetic product 64 | C | B | A | A | A |
| Synthetic product 65 | C | B | A | A | A |
| Synthetic product 66 | C | B | A | A | A |
| Synthetic product 67 | C | B | A | A | A |
| Synthetic product 68 | C | B | B | A | A |
| Synthetic product 69 | C | B | A | A | A |
| Synthetic product 70 | C | B | A | A | A |
| Synthetic product 71 | C | B | B | A | A |
| Synthetic product 72 | C | B | A | A | A |
| Synthetic product 73 | C | B | A | A | A |
| Synthetic product 74 | C | B | A | A | A |
| Synthetic product 75 | C | B | A | A | A |
| Synthetic product 76 | C | B | A | A | A |
| Synthetic product 77 | C | B | A | A | A |
| Synthetic product 78 | C | B | A | A | A |
| Preparation product 12 | C | C | C | C | C |
| Preparation product 16 | C | C | C | C | C |
| Synthetic product 15 | C | C | C | B | B |
| RGD | C | C | C | C | B |
| RGDS | C | C | C | B | B |

(cells/well);
A: not more than 50
B: 51 to 99
C: not less than 100

TABLE 2

Cell Adhesion-Inhibitory effect Against Vitronectin (cells/well)

| Compound Added | Concentration (mg/ml) | | | | |
|---|---|---|---|---|---|
| | 0 | 10 | 50 | 100 | 300 |
| Synthetic product 19-1 | C | A | A | A | A |
| Synthetic product 19-2 | C | A | A | A | A |
| Synthetic product 19-3 | C | A | A | A | A |
| Synthetic product 20 | C | A | A | A | A |
| Synthetic product 21 | C | C | B | B | A |
| Synthetic product 22 | C | A | A | A | A |
| Synthetic product 23 | C | A | A | A | A |
| Synthetic product 24 | C | A | A | A | A |
| Synthetic product 25 | C | A | A | A | A |
| Synthetic product 26 | C | A | A | A | A |
| Synthetic product 27 | C | A | A | A | A |
| Synthetic product 28 | C | B | B | A | A |
| Synthetic product 29 | C | A | A | A | A |
| Synthetic product 30 | C | A | A | A | A |
| Synthetic product 31 | C | B | B | A | A |
| Synthetic product 32 | C | A | A | A | A |
| Synthetic product 33 | C | A | A | A | A |
| Synthetic product 34 | C | A | A | A | A |
| Synthetic product 35 | C | A | A | A | A |
| Synthetic product 36 | C | A | A | A | A |
| Synthetic product 38-1 | C | A | A | A | A |
| Synthetic product 38-2 | C | A | A | A | A |
| Synthetic product 38-3 | C | A | A | A | A |
| Synthetic product 39 | C | A | A | A | A |
| Synthetic product 40 | C | A | A | A | A |
| Synthetic product 41 | C | B | B | A | A |
| Synthetic product 42 | C | C | B | B | A |
| Synthetic product 43 | C | A | A | A | A |
| Synthetic product 44 | C | A | A | A | A |
| Synthetic product 45 | C | A | A | A | A |
| Synthetic product 46 | C | A | A | A | A |
| Synthetic product 47 | C | B | B | A | A |
| Synthetic product 48 | C | A | A | A | A |
| Synthetic product 49 | C | B | A | A | A |
| Synthetic product 50 | C | B | B | A | A |
| Synthetic product 51 | C | A | A | A | A |
| Synthetic product 52 | C | A | A | A | A |
| Synthetic product 53 | C | A | A | A | A |
| Synthetic product 54 | C | A | A | A | A |
| Synthetic product 55 | C | A | A | A | A |
| Synthetic product 56 | C | A | A | A | A |
| Synthetic product 57 | C | A | A | A | A |
| Synthetic product 59-1 | C | A | A | A | A |
| Synthetic product 59-2 | C | A | A | A | A |
| Synthetic product 59-3 | C | A | A | A | A |
| Synthetic product 60 | C | A | A | A | A |
| Synthetic product 61 | C | A | A | A | A |
| Synthetic product 62 | C | C | B | A | A |
| Synthetic product 63 | C | C | B | A | A |
| Synthetic product 64 | C | A | A | A | A |
| Synthetic product 65 | C | A | A | A | A |
| Synthetic product 66 | C | A | A | A | A |

TABLE 2-continued

Cell Adhesion-Inhibitory effect Against Vitronectin (cells/well)

| Compound Added | Concentration (mg/ml) | | | | |
|---|---|---|---|---|---|
| | 0 | 10 | 50 | 100 | 300 |
| Synthetic product 67 | C | A | A | A | A |
| Synthetic product 68 | C | B | B | A | A |
| Synthetic product 69 | C | A | A | A | A |
| Synthetic product 70 | C | A | A | A | A |
| Synthetic product 71 | C | B | B | A | A |
| Synthetic product 72 | C | A | A | A | A |
| Synthetic product 73 | C | A | A | A | A |
| Synthetic product 74 | C | A | A | A | A |
| Synthetic product 75 | C | A | A | A | A |
| Synthetic product 76 | C | A | A | A | A |
| Synthetic product 77 | C | A | A | A | A |
| Synthetic product 78 | C | A | A | A | A |
| Preparation product 12 | C | C | C | C | C |
| Preparation product 16 | C | C | C | C | C |
| Synthetic product 15 | C | C | C | B | B |
| RGD | C | C | C | B | B |
| RGDS | C | C | B | B | A |

(cells/well);
A: not more than 100
B: 101 to 199
C: not less than 200

TEST EXAMPLE 2

Determination of Platelet Coagulation-Inhibitory Activity

The platelet coagulation-inhibitory effect of the compounds of the present invention was assayed, in vitro, using human plasma rich in platelet. The experimental method will be described below.

Experimental Method

To fresh human blood, there was added 1/9 volume of a 3.8% sodium citrate solution, the resulting mixture was centrifuged (1000 rpm; for 10 minutes) and the upper layer was separated as a plasma rich in platelet. The propenamide derivatives, the polymers thereof, the copolymers thereof or salts thereof obtained through lyophilization were dissolved in physiological saline to give a plurality of solutions having various concentrations ranging from 0 to 1.5 mg/ml. Each of the solutions (25 μl) was added to 200 μl of the plasma, incubated at 37° C. for 3 minutes, then a 50 μM of ADP (adenosine diphosphate) solution or a 200 μg/ml collagen solution was added to determine the extent of coagulation in terms of transmittance determined by an aggregometer. The results thus obtained are listed in the following Table 3.

Rate of Coagulation Inhibition=$(1-T/T_0) \times 100\%$ $T_0$: Transmittance observed when the propenamide derivatives, the polymers thereof, the copolymers thereof or salts thereof were not added.

T: Transmittance observed when the propenamide derivatives, the polymers thereof, the copolymers thereof or salts thereof were added.

TABLE 3

Platelet Coagulation-Inhibitory Activity

| Compound Added | IC$_{50}$ (μg/ml) | |
|---|---|---|
| | ADP Stimulation | Collagen Stimulation |
| Synthetic product 19-1 | A | A |
| Synthetic product 19-2 | A | A |
| Synthetic product 19-3 | A | A |
| Synthetic product 20 | A | A |
| Synthetic product 21 | A | A |
| Synthetic product 22 | B | A |
| Synthetic product 23 | B | A |
| Synthetic product 24 | A | A |
| Synthetic product 25 | A | A |
| Synthetic product 26 | A | A |
| Synthetic product 27 | A | A |
| Synthetic product 28 | A | A |
| Synthetic product 29 | A | A |
| Synthetic product 30 | A | A |
| Synthetic product 31 | A | A |
| Synthetic product 32 | A | A |
| Synthetic product 33 | A | A |
| Synthetic product 34 | A | A |
| Synthetic product 35 | A | A |
| Synthetic product 36 | A | A |
| Synthetic product 38-1 | A | A |
| Synthetic product 38-2 | A | A |
| Synthetic product 38-3 | A | A |
| Synthetic product 39 | A | A |
| Synthetic product 40 | A | A |
| Synthetic product 41 | A | B |
| Synthetic product 42 | B | A |
| Synthetic product 43 | A | A |
| Synthetic product 44 | A | A |
| Synthetic product 45 | A | A |
| Synthetic product 46 | A | A |
| Synthetic product 47 | A | B |
| Synthetic product 48 | A | A |
| Synthetic product 49 | B | A |
| Synthetic product 50 | A | A |
| Synthetic product 51 | A | A |
| Synthetic product 52 | A | A |
| Synthetic product 53 | A | A |
| Synthetic product 54 | A | A |
| Synthetic product 55 | A | A |
| Synthetic product 56 | A | A |
| Synthetic product 57 | A | A |
| Synthetic product 59-1 | A | A |
| Synthetic product 59-2 | A | A |
| Synthetic product 59-3 | A | A |
| Synthetic product 60 | A | A |
| Synthetic product 61 | A | A |
| Synthetic product 62 | B | A |
| Synthetic product 63 | B | A |
| Synthetic product 64 | A | A |
| Synthetic product 65 | A | A |
| Synthetic product 66 | A | A |
| Synthetic product 67 | A | A |
| Synthetic product 68 | A | A |
| Synthetic product 69 | A | A |
| Synthetic product 70 | A | A |
| Synthetic product 71 | A | A |
| Synthetic product 72 | A | A |
| Synthetic product 73 | A | A |
| Synthetic product 74 | A | A |
| Synthetic product 75 | A | A |
| Synthetic product 76 | A | A |
| Synthetic product 77 | A | A |
| Synthetic product 78 | A | A |
| Preparation product 12 | C | C |
| Preparation product 14 | C | C |

TABLE 3-continued

Platelet Coagulation-Inhibitory Activity

| Compound Added | IC$_{50}$ ($\mu$g/ml) | |
|---|---|---|
| | ADP Stimulation | Collagen Stimulation |
| Synthetic product 15 | A~B | A~B |
| RGD | A~B | A~B |
| RGDS | A~B | A~B |

IC$_{50}$ ($\mu$g/ml):
A: less than 40
B: 40 to 80
C: more than 80

TEST EXAMPLE 3

Evaluation of Propagation of Animal Cells

The substrates for cultivating animal cells prepared in the working examples and the comparative examples were used to cultivate animal cells. Endothelium cells of blood vessel were cultured in DMEM or 10% fetal calf serum (FCS)-containing DMEM. The animal cells (1×10$^4$ cells/ml) were suspended in the culture media. The suspension was added to a plastic laboratory dish to which the crosslinked polymer or copolymer had previously been added so that the concentration of the cells was 1×10$^4$ cells/cm$^2$. Cultivation was conducted at 37° C. under 5% CO$_2$ atmosphere. After the cultivation, adhesion and propagation were observed under a phase contrast microscope. The results are shown in Table 4.

TABLE 4

Evaluation of propagation of animal cells

| | DMEM | | DMEM/FCS | |
|---|---|---|---|---|
| | Adhesion | Propagation | Adhesion | Propagation |
| Working Example | | | | |
| Synthetic product 37 | A | A | A | A |
| Synthetic product 79 | A | A | A | A |
| Comparative Example | | | | |
| Preparation product 13 | B~C | B~C | A~B | A~B |
| Preparation product 17 | B~C | B~C | A~B | A~B |

Adhesion A: good, B: not good, C: bad
Propagation A: good, B: not good, C: bad

The substrates using Preparation products 13 and 17 were inferior to those using Synthetic products 37 and 79 in both adhesion and propagation in the DMEM not containing FCS.

---

What is claimed is:

1. A copolymer of a propenamide derivative of the general Formula (I) or (II) and a monomer represented by the following general Formula (III), or salts thereof;

Formula (I)

$R^1R^2C{=}CR^3{-}CO{-}\{NH\}{-}\{R^4\}{-}\{CO\}{-}(\{X\}\text{-Arg-Gly-Asp-}\{Y\})_n{-}\{Z\}\text{-H}$;

or

Formula (II)

$H{-}\{CO\}{-}(\{X\}\text{-Arg-Gly-Asp-}\{Y\})_n{-}\{Z\}{-}\{R^5\}{-}\{NH\}{-}CO{-}C(R^3){=}CR^1R^2$ Formula (III)

$H_2C{=}CR{-}\{CO\}{-}\{W\}{-}R^7$ wherein $R^1$ and $R^2$ each is a hydrogen atom or a carboxyl group;

$R^3$ is a hydrogen or halogen atom, methyl, ethyl or carboxymethyl group;

X and Y each is an amino acid residue selected from the group consisting of Ser, Gly, Val, Asn and Pro or a polypeptide consisting of at least two amino acid residues, wherein said amino acid residues are selected from the group consisting of Ser, Gly, Val, Asn and Pro;

Z is —O— or —NH—;

$R^4$ and $R^5$ each is an alkylene group having 1 to 11 carbon atoms or an arylene group having 6 to 11 carbon atoms, further, wherein hydrogen atoms in the alkylene and arylene groups optionally are substituted for with one or more moieties selected from the group consisting of halogen, acyl, aldehyde, carboxyl, amino, hydroxyl, sulfonic acid, aryl, nitro and cyano group;

n is an integer of from 1 to 5;

$R^6$ is a hydrogen atom or a substituted or unsubstituted alkyl group having 1 to 3 carbon atoms;

W is —O— or —NH—;

$R^7$ is a hydrogen atom or an alkyl group having 1 to 12 carbon atoms or an aryl group having 6 to 11 carbon atoms, said alkyl group and said aryl group having at least one member selected from the group consisting of carboxyl, sulfonic acid and phosphoric acid; and the braces signify that each corresponding group or residue therebetween may be present or absent;

wherein the molecular weight of said copolymer is from 3,000 to 300,000 g/mole, and which is obtained by copolymerizing, by radical polymerization, the propenamide derivative and the monomer with a crosslinking agent selected from the group consisting of bismethylacrylate, bisacrylate, bisacrylamide, bismethylacrylamide and divinylbenzene.

2. The copolymer, or salts thereof, of claim 1, wherein the propenamide derivative is present in an amount of from 0.1 to 90 mol % and the crosslinking agent is present in an amount of from 0.1 to 30 mol %.

3. A copolymer of a propenamide derivative of the general Formula (I) or (II) and a monomer represented by the following general Formula (IV) or salts thereof;

Formula (I)

R$^1$R$^2$C=CR$^3$—CO—{NH}—{R$^4$}—{CO}—({X}-Arg-Gly-Asp-{Y})$_n$-{Z}-H;

or

Formula (II)

H—{CO}—({X}-Arg-Gly-Asp-{Y})$_n$-{Z}-{R$^5$}—{NH}—CO—C(R$^3$)=CR$^1$R$^2$

Formula (IV)

H$_2$C=CR—{CO}-{W}-R$^9$ wherein R$^1$ and R$^2$ each is a hydrogen atom or a carboxyl group;

R$^3$ is a hydrogen or halogen atom, methyl, ethyl or carboxymethyl group;

X and Y each is an amino acid residue selected from the group consisting of Ser, Gly, Val, Asn and Pro or a polypeptide consisting of at least two amino acid residues, wherein said amino acid residues are selected from the group consisting of Ser, Gly, Val, Asn and Pro;

Z is —O— or —NH—;

R$^4$ and R$^5$ each is an alkylene group having 1 to 11 carbon atoms or an arylene group having 6 to 11 carbon atoms, further, wherein hydrogen atoms in the alkylene and arylene groups optionally are substituted for with one or more moieties selected from the group consisting of halogen, acyl, aldehyde, carboxyl, amino, hydroxyl, sulfonic acid, aryl, nitro and cyano group;

n is an integer of from 1 to 5;

R$^8$ is a hydrogen atom or a substituted or unsubstituted alkyl group having 1 to 3 carbon atoms, wherein the substituted alkyl group is substituted with one or more of halogen, acyl, aldehyde, amino, hydroxyl, nitro or cyano groups;

W is —O— or —NH—;

R$^9$ is an alkyl group having 1 to 12 carbon atoms or an aryl group having 6 to 12 carbon atoms, said alkyl group and said aryl group having at least one member selected from the group consisting of primary amino, N-alkyl amino, N,N-dialkylamino, unsubstituted imino, amidino, quaternary ammonium and ammonium groups; and the braces signify that each corresponding group or residue therebetween may be present or absent;

wherein the molecular weight of said copolymer is from 3,000 to 300,000 g/mole, and which is obtained by copolymerizing, by radical polymerization, the propenamide derivative and the monomer with a crosslinking agent selected from the group consisting of bismethylacrylate, bisacrylate, bisacrylamide, bismethylacrylamide and divinylbenzene.

4. The copolymer, or salts thereof, of claim 1, wherein the propenamide derivative is present in an amount of from 0.1 to 90 mol % and the crosslinking agent is present in an amount of from 0.1 to 30 mol %.

5. A copolymer of a propenamide derivative of the general Formula (I) or (II) and an anionic monomer represented by the following general Formula (III) or salts thereof;

Formula (I)

R$^1$R$^2$C=CR$^3$—CO—{NH}—{R$^4$}—{CO}—({X}-Arg-Gly-Asp-{Y})$_n$-{Z}-H;

or

Formula (II)

H—{CO}—({X}-Arg-Gly-Asp-{Y})$_n$-{Z}-{R$^5$}—{NH}—CO—C(R$^3$)=CR$^1$R$^2$

Formula (III)

H$_2$C=CR—{CO}-{W}-R$^7$ wherein R$^1$ and R$^2$ each is a hydrogen atom or a carboxyl group, R$^3$ is a hydrogen or halogen atom, methyl, ethyl or carboxymethyl group, X and Y each is an amino acid residue selected from the group consisting of Ser, Gly, Val, Asn and Pro or a polypeptide consisting of at least two amino acid residues, wherein said amino acid residues are selected from the group consisting of Ser, Gly, Val, Asn and Pro;

Z is —O— or —NH—;

R$^4$ and R$^5$ each is an alkylene group having 1 to 11 carbon atoms or an arylene group having 6 to 11 carbon atoms, further, wherein hydrogen atoms in the alkylene and arylene groups optionally are substituted for with one or more moieties selected from the group consisting of halogen, acyl, aldehyde, carboxyl, amino, hydroxyl, sulfonic acid, aryl, nitro and cyano group;

n is an integer of from 1 to 5;

R$^6$ is a hydrogen atom, a substituted or unsubstituted alkyl group having 1 to 3 carbon atoms;

W is —O— or —NH—;

R$^7$ is a hydrogen atom or a substituted or unsubstituted alkyl group having 1 to 12 carbon atoms or a substituted or unsubstituted aryl group having 6 to 11 carbon atoms, wherein the substituted alkyl and the substituted aryl group is substituted by at least one member selected from the group consisting of carboxyl, sulfonic acid and phosphoric acid; and the braces signify that each corresponding group or residue therebetween may be present or absent;

wherein the molecular weight of said copolymer is from 3,000 to 300,000 g/mole.

6. The copolymer of claim 5, wherein the molecular weight of said polymer is in the range of from about 3,000 to 200,000 (g/mole).

7. The copolymer of claim 5, wherein the propenamide derivative is present in an amount of from 0.1 to 90 mol %.

8. A copolymer of a propenamide derivative of the general Formula (I) or (II) and a cationic monomer represented by the following general Formula (IV) or salts thereof:

Formula (I)

R$^1$R$^2$C=CR$^3$—CO—{NH}—{R$^4$}—{CO}—({X}-Arg-Gly-Asp-{Y})$_n$-{Z}-H;

or

Formula (II)

H—{CO}—({X}-Arg-Gly-Asp-{Y})$_n$-{Z}-{R$^5$}—{NH}—CO—C(R$^3$)=CR$^1$R$^2$

Formula (IV)

H$_2$C=CR$^8$—{CO}-{W}-R$^9$ wherein R$^1$ and R$^2$ each is a hydrogen atom or a carboxyl group, R$^3$ is a hydrogen or halogen atom, methyl, ethyl or carboxymethyl group, X and Y each is an amino acid residue selected from the group consisting of Ser, Gly, Val, Asn and Pro or a polypeptide consisting of at least two amino acid residues, wherein said amino acid residues are selected from the group consisting of Ser, Gly, Val, Asn and Pro;

Z is —O— or —NH—;

$R^4$ and $R^5$ each is an alkylene group having 1 to 11 carbon atoms or an arylene group having 6 to 11 carbon atoms, further, wherein hydrogen atoms in the alkylene and arylene groups optionally are substituted for with one or more moieties selected from the group consisting of halogen, acyl, aldehyde, carboxyl, amino, hydroxyl, sulfonic acid, aryl, nitro and cyano group;

n is an integer of from 1 to 5;

$R^8$ is a hydrogen atom or a substituted or unsubstituted alkyl group having 1 to 3 carbon atoms, wherein the substituted alkyl group is substituted with one or more of halogen, acyl, aldehyde, amino, hydroxyl, nitro or cyano groups;

W is —O— or —NH—;

$R^9$ is a substituted or unsubstituted alkyl group having 1 to 12 carbon atoms, or a substituted or unsubstituted aryl group having 6 to 12 carbon atoms, wherein the substituted alkyl and the substituted aryl group is substituted by at least one member selected from the group consisting of primary amino, N-alkyl amino, N,N-dialkylamino, unsubstituted imino, amidino, quaternary ammonium and ammonium groups; and the braces "{}" signify that each corresponding group or residue therebetween may be present or absent;

wherein the molecular weight of said copolymer is from 3,000 to 300,000 g/mole.

9. The copolymer of claim 8, wherein the molecular weight of said polymer is in the range of from about 3,000 to 200,000 g/mole.

10. The copolymer of claim 8, wherein the propenamide derivative is present in an amount of from 0.1 to 90 mol %.

11. A composition for inhibiting adhesion of animal cells, which comprises:

(A) a pharmaceutically effective amount of at least one member selected from the group consisting of a copolymer of claim 5 and a copolymer of claim 8; and (B) at least one member from the group consisting of pharmaceutically acceptable excipients, carriers, and diluents.

12. A composition for inhibiting coagulation of blood platelets, which comprises (A) a pharmaceutically effective amount of at least one member selected from the group consisting of a copolymer of claim 5 and a copolymer of claim 8; and (B) at least one member from the group consisting of pharmaceutically acceptable excipients, carriers, and diluents.

13. A substrate for cultivating animal cells, which comprises as an effective component at least one member selected from the group consisting of a copolymer of claim 5 and a copolymer of claim 8.

14. A propenamide derivative selected from the group consisting of $H_2C$=CH—CO—NH—$CH_2CH_2$—CO-Arg-Gly-Asp-Ser and $H_2C$=C($CH_3$)—CO—NH—$CH_2CH_2$—CO-Arg-Gly-Asp-Ser.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:1:

Xaa Arg Gly Asp
1

(2) INFORMATION FOR SEQ ID NO:2:

(i) SEQUENCE CHARACTERISTICS:
      (A) LENGTH: 7 amino acids
      (B) TYPE: amino acid
      (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:2:

Ala Arg Gly Asp Arg Gly Asp
1               5

(2) INFORMATION FOR SEQ ID NO:3:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:3:

Ala Arg Gly Asp Arg Gly Asp Arg Gly Asp
1               5                   10

(2) INFORMATION FOR SEQ ID NO:4:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:4:

Ala Arg Gly Asp Arg Gly Asp Arg Gly Asp Arg Gly Asp Arg Gly
1               5                   10                  15
Asp
16

(2) INFORMATION FOR SEQ ID NO:5:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:5:

Xaa Arg Gly Asp Ser Gly
1               5

(2) INFORMATION FOR SEQ ID NO:6:

(i) SEQUENCE CHARACTERISTICS:
        (A) LENGTH: 5 amino acids
        (B) TYPE: amino acid (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:6:

Xaa Arg Gly Asp Ser
1               5

(2) INFORMATION FOR SEQ ID NO:7:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:7:

Leu Arg Gly Asp Ser
1               5

(2) INFORMATION FOR SEQ ID NO:8:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:8:

Gln Arg Gly Asp Ser
1               5

(2) INFORMATION FOR SEQ ID NO:9:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:9:

Xaa Gly Arg Gly Asp Ser
1               5

```
(2) INFORMATION FOR SEQ ID NO:10:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:10:

Gly Arg Gly Asp Ser Pro
1               5

(2) INFORMATION FOR SEQ ID NO:11:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:11:

Gly Gly Gly Arg Gly Asp Ser
1               5

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:12:

Ala Arg Gly Asp Ser
1               5

(2) INFORMATION FOR SEQ ID NO:13:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:13:
```

```
Ala Arg Gly Asp Ser Gly
1               5

(2) INFORMATION FOR SEQ ID NO:14:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:14:

Arg Gly Asp Gly
1

(2) INFORMATION FOR SEQ ID NO:15:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:15:

Ala Arg Gly Asp Gly
1             5
```